US012584160B2

(12) United States Patent
Xue et al.

(10) Patent No.: US 12,584,160 B2
(45) Date of Patent: Mar. 24, 2026

(54) METHOD FOR CAPTURING RNA IN SITU HIGHER-ORDER STRUCTURES AND INTERACTIONS

(71) Applicant: Institute of Biophysics, Chinese Academy of Sciences, Beijing (CN)

(72) Inventors: Yuanchao Xue, Beijing (CN); Zhaokui Cai, Beijing (CN); Changchang Cao, Beijing (CN)

(73) Assignee: Institute of Biophysics, Chinese Academy of Sciences, Beijing (CN)

( * ) Notice: Subject to any disclaimer, the term of this patent is extended or adjusted under 35 U.S.C. 154(b) by 1338 days.

(21) Appl. No.: 17/297,414

(22) PCT Filed: Jul. 5, 2019

(86) PCT No.: PCT/CN2019/094790
§ 371 (c)(1),
(2) Date: May 26, 2021

(87) PCT Pub. No.: WO2020/224040
PCT Pub. Date: Nov. 12, 2020

(65) Prior Publication Data
US 2022/0033807 A1      Feb. 3, 2022

(30) Foreign Application Priority Data

May 9, 2019    (CN) ......................... 201910384194.2

(51) Int. Cl.
*C12Q 1/6869*          (2018.01)
*C12N 15/10*          (2006.01)
*C12Q 1/6806*          (2018.01)

(52) U.S. Cl.
CPC ....... *C12Q 1/6806* (2013.01); *C12N 15/1065* (2013.01); *C12Q 1/6869* (2013.01)

(58) Field of Classification Search
CPC . C12Q 1/6806; C12Q 1/6869; C12N 15/1065
See application file for complete search history.

(56) References Cited

U.S. PATENT DOCUMENTS

2019/0390266 A1* 12/2019 Sharp ................. C12Q 1/6855

FOREIGN PATENT DOCUMENTS

| CN | 102628038 A | * | 8/2012 |
|----|-------------|---|--------|
| CN | 108300767 A | | 7/2018 |
| CN | 109505012 A | | 3/2019 |
| WO | WO-2019/071262 A1 | | 4/2019 |

OTHER PUBLICATIONS

Booy et al. (RNA, 291;10, 5355-5372 (Year: 2016).*
Kaewsapsak et al., eLife 6: e29224 (Year: 2017).*
Kore et al., Nucleosides, Nucleotides & Nucleic Acids, 28;4 (Year: 2009).*
Nguyen et al., Nature Communications, 7;12023 (Year: 2016).*
Nilsen, Cold Spring Harbor Protocols 2014.9, 2014: pdb-prot080879 (Year: 2014).*
Ramani et al., Nat Biotechnol., 3;33(9) (Year: 2015).*
Moritz B. et al.; "Simple Methods for the 3' biotinylation of RNA"; RNA, Cold Spring Harbor Laboratory Press, US; vol. 20, Issue No. 3, Mar. 2014, published online Jan. 21, 2014; pp. 421-427 (XP-055354650).

* cited by examiner

*Primary Examiner* — Heather Calamita
(74) *Attorney, Agent, or Firm* — MUNCY, GEISSLER, OLDS & LOWE, P.C.

(57) ABSTRACT

The present invention discloses a method for capturing an RNA in situ higher-order structure and interaction. The method includes: fixing protein-mediated RNA-RNA interaction in cell or tissue; performing membrane permeabilization while keeping the cell intact; degrading free RNA; labeling the 3' end of the RNA with pCp-biotin and performing proximal ligation in situ; purifying the chimeric RNA containing the pCp-biotin after the cell is digested; constructing the strand-specific library; and performing high-throughput sequencing. In the present invention, under the condition of not destroying the cell structure and keeping the integrity of cell, treat the intracellular RNA in situ, and capture RNA intra- and intermolecular interactions in a physiological state; the 3' end of the RNA is labeled with the pCp-biotin, and in situ ligation is performed under non-denaturing conditions, thereby greatly improving the labeling efficiency and reducing intermolecular specific ligation; and the chimeric RNA labeled with C-biotin is enriched by C1 magnetic beads, so that the fraction of effective sequencing data is increased, and the sequencing cost is reduced.

3 Claims, 6 Drawing Sheets
Specification includes a Sequence Listing.

METHOD FOR CAPTURING RNA IN SITU HIGHER-ORDER STRUCTURES AND INTERACTIONS

FIELD OF THE INVENTION

The present invention relates to the field of biotechnology, in particular to a method for capturing RNA in situ higher-order structures and interactions.

BACKGROUND OF THE INVENTION

DNA, the carrier of genetic information, needs to be transcribed into RNA and then translated into protein in order to perform biological functions. As a transmitter of the genetic information, the RNA is mainly used for encoding and guiding the synthesis of proteins. This type of protein-encoding RNAs is collectively referred to as messenger RNA (mRNA). In addition, the human genome has also been transcribed to produce a large number of RNAs that do not encode proteins, and this type of RNAs is called noncoding RNA (ncRNA). The non-coding RNAs with regulatory functions that have been discovered so far include: tRNA, rRNA, siRNA, miRNA, piRNA, snoRNA, circRNA, lncRNA, and so on. Their abnormal expression and mutation are related to numerous diseases such as cancer occurrence, development and reproductive defects. As a key regulator of genetic information, the RNA often needs to form a complex higher-order structure through intramolecular base-pairing, and then interacts with other RNA molecules to perform important biological regulatory functions. By using the sequencing technology, we can already obtain detailed sequence information of the RNA, but the structure of the RNA, especially the acquisition of the higher-order structural information, is still a worldwide problem. Although some physical methods, such as nuclear magnetic resonance, cryo-electron microscopy and crystallography, can analyze the high-resolution structure and intramolecular and intermolecular interactions of the RNA, the throughput of these technologies is too low. At present, the high-resolution structures of human RNAs included in the international protein database PDB are few. Therefore, how to systematically and accurately analyze the intramolecular and intermolecular interactions of the RNA is still a huge challenge we face.

In recent years, a large number of techniques for analyzing the secondary structure of the RNA have been developed. These techniques are characterized by firstly using chemical modification or enzymatic digestion to treat the RNA, and then performing library construction and sequencing, for example: DMS-seq, Structure-seq, icSHAPE, and so on, they take advantage of the feature that the RNA in single-stranded region is easily modified by the compound DMS (dimethyl sulfate) or NAI-N3, and they deduce which bases of the RNA are in the single-stranded region by analyzing where the reverse transcriptase stops. In addition, for double-stranded region in the RNA structure, there are currently many methods available for analysis, for example, PARIS, LIGR-seq, SPLASH, and so on. The basic principle of these three methods is: Psoralen or AMT is added into the culture medium, they can pass through the cell membrane and quickly bind to the double-strand region on the RNA, after being irradiated with 254 nm ultraviolet (UV), the paired RNAs in the cell will be covalently cross-linked by the Psoralen or AMT, and then the enriched RNA is fragmented and proximally ligated in a solution. Then the ligated RNA is irradiated with 365 nm UV, covalent bond between the Psoralen or AMT and the double-stranded RNA can be decrosslinked, and then library construction and sequencing are performed. Although the above methods can probe the single-stranded and double-stranded regions of the RNA with high throughput, they also have some disadvantages: first, they cannot capture non-Watson-Crick base-pairings and long-range RNA loop-loop interactions. Second, these ligation reactions are all carried out in the solution, and there are non-specific ligations, which cannot reflect the true structure of the RNA in the cell, resulting in a large number of false-positive intermolecular ligations. Third, in the data obtained from sequencing, the ratio of chimeric reads (that is, the product of ligation between different RNA fragments) is low, and there are too many useless data. The RNA proximal ligation technology (RPL) can theoretically overcome the above technical defects, but due to the lack of cross-linking and chimeric RNA enrichment, the RPL technology can only identify intramolecular interactions, but cannot identify intermolecular RNA-RNA interactions.

In recent years, high-throughput transcriptome sequencing indicates that more than 90% of the genome is transcribed, resulting in a large number of non-coding RNAs, some of which are tightly bound to chromatin, such as lncRNA (long non-coding RNA). The lncRNA is a type of RNA that has a length of more than 200 nt and does not encode proteins. At present, the number of human lncRNAs included in the NONCODE database has exceeded 160,000, which is 8 times greater than that of protein-encoding genes, but the functions, targets and mechanisms of most of the noncoding RNAs are still unclear. The commonly used methods for identifying lncRNA targets include: CHIRP, CHART, and RAP. The principle of these methods is: under physiological conditions, first treating the cell with formaldehyde to fix RNAs and interacting target molecules thereof; then lysing the cell, and performing fragmentation on the chromatin by using ultrasound or enzymes; then enriching DNA fragments that interact with the target RNA by using biotin-modified DNA probes; after adding adapters to the DNA fragments, performing library amplification and high-throughput sequencing by using PCR; and finally identifying the target DNA that interacts with specific lncRNA in combination with bioinformatics analysis. The CHIRP, CHART, and RAP methods only focus on the DNA targets, but ignore RNA target sites with important functions, and can only identify all potential DNA targets of one lncRNA (one to all) in the cell at one time, such that the throughput is too low. Therefore, how to systematically identify all binding sites of all lncRNAs in the cell genome-wide is still a difficult problem.

SUMMARY OF THE INVENTION

In view of the problems of the above technologies, the present invention develops a new technology of RNA in situ conformation sequencing (RIC-seq for short). The basic principle is to perform formaldehyde cross-linking on cells to fix protein-mediated RNA-RNA proximal interaction and to perforate the cell membrane while keeping the cell intact, and then treat cells with micrococcal nuclease (MNase) to remove free RNA fragments that are not protected by protein, then pCp-biotin labeling is performed on the 3' end of RNAs, and proximal ligation is performed in situ. After digesting cells with proteinase K, chimeric RNAs containing C-biotin are purified, and the strand-specific library is constructed. This step greatly increases the percentage of chimeric reads in data, reduces useless data and sequencing cost. The RIC-seq performs in situ ligation of RNA-RNA under the condition of maintaining the integrity of the cell, all direct RNA-RNA proximal contacts can be captured simultaneously, and RNA binding targets of all lncRNAs in vivo can be detected in situ (all to all). The most important thing is to be able to reconstruct the higher-order structure of the RNA based on the proximal spatial distance information of the RNA.

In the first aspect, the present invention claims a method for capturing an RNA higher-order structure in situ and/or verifying in situ RNA-RNA interaction (i.e., a RIC-seq method).

The method for capturing the RNA higher-order structure in situ and/or verifying the in situ RNA-RNA interaction (the RIC-seq method) claimed in the present invention may include the following steps:

(1) Treating cells or tissue sample to fix protein-mediated RNA-RNA proximal interaction, wherein the volume of the tissue sample may be 1 cubic centimeter; the close range may be within 50 angstroms.

(2) Performing membrane permeabilization (cell membrane and nuclear membrane permeabilization) while keeping the cell intact.

(3) Degrading the free RNAs that are not protected by protein.

(4) Labeling the 3' end of the RNA protected by the protein with a "pCp-Marker 1" and performing proximal ligation in situ, wherein the proximal end may be within 50 angstroms.

Wherein, the "pCp-Marker 1" is a cytosine nucleotide with phosphate groups at both ends and labeled with the maker 1. Correspondingly, a "Cp-marker" appearing below is a cytosine nucleotide with a phosphate group at the 3' end and labeled with the marker 1; and a "C-marker 1" is a cytosine nucleotide labeled with the marker 1.

In a specific embodiment of the present invention, the "pCp-marker 1" is specifically pCp-biotin. Correspondingly, the "Cp-marker 1" is specifically Cp-biotin; and the "C-marker 1" is specifically C-biotin.

The pCp-biotin is a cytosine nucleotide with phosphate groups at both ends and labeled with biotin. Correspondingly, the Cp-biotin appearing below is a cytosine nucleotide with a phosphate group at the 3' end and labeled with the biotin; and C-biotin is a cytosine nucleotide labeled with the biotin.

(5) Purifying the chimeric RNA (i.e., a product of ligation between different RNA fragments) containing the "C-marker 1" after the cells are digested; and constructing the strand-specific library.

(6) Performing high-throughput sequencing.

Before the step (1) of the method, the method can also include a step of washing the cell or tissue sample. The washing method can be specifically carried out as follows: adding precooling PBS solution (pH 7.4) into the cell or tissue sample for washing, and performing centrifugation at 4° C. and 2500 rpm for 10 minutes to remove the PBS solution to obtain the washed cell sample.

In the step (1) of the method, treatment for cell or tissue sample is to perform formaldehyde cross-linking on the cell or tissue sample.

Further, the step (1) can be performed according to a method including the following steps:

(a1) placing the cell or tissue sample in a formaldehyde solution at room temperature for 10 minutes, wherein the formaldehyde solution is a formaldehyde solution with a percent by volume of 1% (the solvent is PBS solution).

Furthermore, after the step (a1), the method may further include the following step (a2):

(a2) adding the glycine solution into the cell or tissue sample treated in the step (a1) to terminate the reaction, uniformly mixing, and incubating for 10 minutes at room temperature, wherein the glycine solution is a glycine solution with a concentration of 0.125 mol/L (the solvent is DEPC water).

In the step (2) of the method, a permeabilization solution used during the membrane permeabilization is the Permeabilization solution.

Further, the step (2) can be performed according to a method including the following steps:

(b1) placing the cell or tissue sample treated in the step (1) in the Permeabilization solution at 0° C.-4° C. (such as an ice bath) for 15 minutes, and uniformly mixing it every 2 minutes, wherein the solvent of the Permeabilization solution is a 10 mM of Tris-HCl buffer with pH 7.5, and the solute and concentration are as follows: 10 mM of NaCl, 0.5% (v/v) NP-40, 0.3% (v/v) Triton X-100, 0.1% (v/v) Tween 20, 1×protease inhibitors and 2 U/ml of SUPERase·In™ RNase Inhibitor.

In a specific embodiment of the present invention, the 1×protease inhibitors is specifically a Sigma product with the catalog number of P8340-5ML (the specific components include AEBSF, Aprotinin, Bestatin, E-64, Leupeptin and Pepstatin A). Of course, the 1×protease inhibitors can also be other products with the same components.

In a specific embodiment of the present invention, the SUPERase.In™ RNase Inhibitor is a Thermo Fisher product with the catalog number of AM2694. Of course, the SUPERase.In™ RNase Inhibitor can also be other products with the same components.

Furthermore, after the step (b1), the method can further include the following step (b2):

(b2) washing the cell or tissue sample treated in the step (b1) with the 1×PNK solution, wherein the solvent of the 1×PNK solution is 50 mM of Tris-HCl buffer with pH 7.4, and the solute and concentration are as follows: 10 mM of MgCl₂, 0.1 mg/ml of BSA, and 0.2% (v/v) NP-40.

In the step (b2), the washing may be multiple times of washing, such as 3 times. Each washing can include the following steps: performing uniform mixing for 5 minutes at 4° C. by rotating (such as 20 rpm), and performing centrifugation at 4° C. and 3500 rpm for 5 minutes to remove the washing solution.

In the step (3) of the method, MNase is used for achieving the "degrading the free RNAs that are not protected by protein".

Further, the step (3) can be performed according to a method including the following steps:

(c1) placing the sample treated in the step (2) in the 1×MNase solution for reaction, wherein the concentration of the MNase in the 1×MNase solution can be 0.03 U/µl. The conditions of the reaction can be: incubating at 37° C. for 10 minutes, and shaking at 1000 rpm for 15 seconds every 2 minutes.

Furthermore, after the step (c1), the method can further include the following step (c2):

(c2) washing the sample treated in the step (c1) with 1×PNK+EGTA solution and 1×PNK solution, wherein the solvent of the 1×PNK+EGTA solution is 50 mM of Tris-HCl buffer with pH 7.4, and the solute and concentration are as follows: 20 mM of EGTA, and 0.5% (v/v) NP-40. The solvent of the 1×PNK solution is 50 mM of Tris-HCl buffer with pH 7.4, and the solvent and concentration are as follows: 10 mM of MgCl$_2$, 0.1 mg/ml of BSA, and 0.2% (v/v) NP-40.

In the step (c2), the washing can be multiple times of washing, for example, washing with the 1×PNK+EGTA solution twice, and washing with the 1×PNK solution twice. Each washing can include the following steps: performing uniform mixing for 5 minutes at 4° C. by rotating (such as 20 rpm), and performing centrifugation at 4° C. and 3500 rpm for 5 minutes to remove the washing solution.

In the method, the step (4) can be performed according to a method including the following steps:

(d1) hydroxylating the 3' end of the RNA protected by the protein. Further, by treating the sample treated in the step (3) with the alkaline phosphatase, the 3' end of the RNA protected by the protein can be hydroxylated; and furthermore, during the process of "treating the sample treated in the step (3) with the alkaline phosphatase", the content of the alkaline phosphatase in the reaction system can be 0.1 U/µl. The reaction conditions can be as follows: incubating at 37° C. for 10 minutes, and shaking at 1000 rpm for 15 seconds every 3 minutes.

Still further, the step (d1) can also include a washing step after the reaction is completed; the washing specifically includes successively using the 1×PNK+EGTA solution (the formula is the same as above), the high-salt solution and the 1×PNK solution to wash the cell sample successively. The solvent of the high-salt solution is 5×PBS (no Mg$^{2+}$, Ca$^{2+}$) (that is, 5×PBS buffer (pH 7.4): 685 mmol/L of NaCl, 13.5 mmol/L of KCl, 50 mmol/L of Na$_2$HPO$_4$, and 10 mmol/L of KH$_2$PO$_4$), and the solute and concentration are 0.5% (v/v) NP-40. The solvent of the 1×PNK solution is 50 mM of Tris-HCl buffer with pH 7.4, and the solvent and concentration are as follows: 10 mM of MgCl$_2$, 0.1 mg/ml of BSA, and 0.05% (v/v) NP-40. Wherein, the washing can be multiple times of washing, for example, washing with the 1×PNK+EGTA solution twice, washing with the high-salt solution twice, and washing with the 1×PNK solution twice. Each washing can include the following steps: performing uniform mixing for 5 minutes at 4° C. by rotating (such as 20 rpm), and performing centrifugation at 4° C. and 3500 rpm for 5 minutes to remove the washing solution.

(d2) labeling the 3' end of the RNA with Cp-biotin.

Further, the pCp-biotin can be added to the sample treated in the step (d1) to perform a ligation reaction, so that the 3' end of the RNA is labeled with Cp-biotin.

Furthermore, the enzyme used in the ligation reaction can be the T4 RNA ligase. In the reaction system, the final concentration of the pCp-biotin can be 40 m; and the final concentration of the T4 RNA ligase can be 1 U/µl. The reaction conditions can be as follows: incubating at 16° C. for 12-16 hours, and shaking at 1000 rpm for 15 seconds every 3 minutes.

Still further, the step (d2) can also include a washing step after the reaction is completed; the washing specifically includes successively using the 1×PNK solution (reference can be made to embodiment 1 in the Detailed Description of the Embodiments for the formula) to wash the cell sample successively; wherein, the washing can be multiple times of washing, for example, three times. Each washing can include the following steps: performing uniform mixing for 5 minutes at 4° C. by rotating (such as 20 rpm), and performing centrifugation at 4° C. and 3500 rpm for 5 minutes to remove the washing solution.

(d3) converting the phosphate group in Cp-biotin at the 3' end of the RNA into a hydroxyl group.

Further, treating the sample treated in the step (d2) with the alkaline phosphatase to convert the phosphate group in the Cp-biotin at the 3' end of the RNA into the hydroxyl group; and furthermore, during the process of "treating the sample treated in the step (d2) with the alkaline phosphatase", the content of the alkaline phosphatase in the reaction system can be 0.1 U/µl. The reaction conditions can be as follows: incubating at 37° C. for 10 minutes, and shaking at 1000 rpm for 15 seconds every 3 minutes.

Still further, the step (d3) can also include a washing step after the reaction is completed; the washing can specifically include successively using the 1×PNK+EGTA solution (the formula is the same as above), the high-salt solution (the formula is the same as above) and the 1×PNK solution (the formula is the same as the step (d1) to wash the cell sample successively. Wherein, the washing can be multiple times of washing, for example, washing with the 1×PNK+EGTA solution twice, washing with the high-salt solution twice, and washing with the 1×PNK solution twice. Each washing can include the following steps: performing uniform mixing for 5 minutes at 4° C. by rotating (such as 20 rpm), and performing centrifugation at 4° C. and 3500 rpm for 5 minutes to remove the washing solution.

(d4) phosphorylating the 5' end of the RNA.

Further, treating the sample treated in the step (d3) with the T4 PNK enzyme to phosphorylate the 5' end of the RNA.

Furthermore, during the process of "treating the sample treated in the step (d3) with the T4 PNK enzyme", the content of the T4 PNK enzyme in the reaction system can be 1 U/µl. The reaction conditions can be as follows: incubating at 37° C. for 45 minutes, and shaking at 1000 rpm for 15 seconds every 3 minutes.

Still further, the step (d4) can also include a washing step after the reaction is completed; the washing can specifically include successively using the 1×PNK+EGTA solution (the formula is the same as above) and the 1×PNK solution (the formula is the same as the step (d1) for washing. Wherein, the washing may be multiple times of washing, for example, washing with the 1×PNK+EGTA solution twice, and washing with the 1×PNK solution twice. Each washing can include the following steps: performing uniform mixing for 5 minutes at 4° C. by rotating (such as 20 rpm), and performing centrifugation at 4° C. and 3500 rpm for 5 minutes to remove the washing solution.

(d5) performing proximal ligation in situ, wherein the proximal end can be within 50 angstroms.

Further, by adding the T4 RNA ligase into the sample treated in the step (d4), the proximal ligation is realized in situ.

Furthermore, during the process of "adding the T4 RNA ligase into the sample treated in the step (d4)", the content of the T4 RNA ligase in the reaction system can be 0.5 U/µl. The reaction conditions can be as follows: incubating at 16° C. for 12-16 hours, and shaking at 1000 rpm for 15 seconds every 3 minutes.

Still further, the step (d2) can also include a washing step after the reaction is completed; the washing can specifically include successively using the 1×PNK solution (the formula is the same as above) to wash the cell sample. Wherein, the washing may be multiple times of washing, for example, three times. Each washing can include the following steps: performing uniform mixing for 5 minutes at 4° C. by rotating (such as 20 rpm), and performing centrifugation at 4° C. and 3500 rpm for 5 minutes to remove the washing solution.

In the method, the step (5) can be performed according to a method including the following steps:

(e1) using the proteinase K to digest the cell.

Further, during the process of "using the proteinase K to digest the cell", the content of the proteinase K in the reaction system can be 0.12 U/μl. The reaction conditions can be as follows: incubating at 37° C. for 60 minutes, and incubating at 56° C. for 15 minutes.

(e2) extracting total RNA, and performing fragmentation treatment.

In the step, the total RNA can be extracted by using TRIzol LS and chloroform. In addition, 500 μl of isopropanol and 15 μg of glycoblue can be added when the RNA is precipitated overnight at −20° C.

Further, after the total RNA is extracted, the steps of removing genomic DNA (such as treatment with DNase I) and removing ribosome RNA (such as removing the ribosome RNA by using probes base-paired with the ribosome RNA) can also be included.

Wherein, the steps of removing the ribosome RNA by using the DNA probe base-paired with the ribosome RNA can be as follows: adding ribosome RNA probe with the same mass into the RNA, incubating at 95° C. for 2 minutes, cooling to 22° C. at a speed of 0.1° C./s, and incubating at 22° C. for 5 minutes. (The sample can be put on ice immediately after the reaction is completed). Degrading the RNA: degrading the RNA in an RNA hybrid strand (such as adding RNase H), and degrading the DNA probe (such as adding Turbo DNase). Then, purifying the RNA (such as using the Zymo RNA clean kit).

In the step, the fragmentation treatment of the RNA may specifically adopt an alkaline lysis method. In a specific embodiment of the present invention, the 1×first strand buffer (formulation: 50 mM of Tris-HCl, pH 8.3; 75 mM of KCl; 3 mM of MgCl$_2$) is used, and the fragmentation treatment is performed on the RNA in a PCR thermal cycler at 94° C. for 5 minutes.

(e3) enriching the chimeric RNA labeled with "C-marker 1" (such as C-biotin) by using the magnetic bead on which the marker 2 is fixed; and the marker 2 can specifically bind to the marker 1.

In a specific embodiment of the present invention, the marker 1 is specifically biotin, and the marker 2 is specifically streptavidin. The magnetic bead on which the marker 2 is fixed is streptavidin magnetic bead.

In this step, before enriching the chimeric RNA labeled with C-biotin by using the streptavidin magnetic bead, a step of blocking the streptavidin magnetic bead is also included. The specific steps can be as follows: taking 20 μl of C1 magnetic beads, placing a centrifuge tube on a magnetic stand, sucking out the supernatant after the solution is clear, adding 20 μl of solution A, resuspending the magnetic beads, incubating at room temperature for 2 minutes, putting the centrifuge tube on the magnetic stand, removing the supernatant after the solution is clear, repeating this step once, adding 20 μl of solution B, resuspending the magnetic beads, putting the centrifuge tube on the magnetic stand, removing the supernatant after the solution is clear, adding 32 μl of yeast RNA (50 μg), 68 μl of DEPC water and 100 μl of 2×TWB solution, resuspending the magnetic beads, putting the centrifuge tube on a rotary mixer, uniformly mixing for 1 hour by rotating, then putting the centrifuge tube on the magnetic stand, removing the supernatant after the solution is clear, adding 500 μl of 1×TWB solution, resuspending the magnetic beads, putting the centrifuge tube on the magnetic stand, removing the supernatant after the solution is clear, and repeating this step twice.

In this step, after enriching the chimeric RNA labeled with C-biotin by using the streptavidin magnetic bead, a step of eluting the RNA from the magnetic bead is also included.

(e4) constructing the strand-specific library.

The step mainly includes: synthesizing the first-stranded cDNA; synthesizing the second-stranded DNA; repairing the tail end of dsDNA; adding 'A' to the DNA with the tail end repaired; ligating an adapter; performing PCR amplification by using the DNA with the ligated adapter as the template, recycling the PCR product of specific fragment size on an agarose gel to obtain the strand-specific library; and performing high-throughput sequencing. These steps are all routine operations in the field. For the method of constructing the strand-specific library according to the conventional procedures, reference can be made to related recordings in "Levin, J Z, Yassour, M., Adiconis, X., Nusbaum, C., Thompson, D A, Friedman, N., Gnirke, A., and Regev, A. (2010). Comprehensive comparative analysis of strand-specific RNA sequencing methods. Nature methods 7, 709-715."

In the specific embodiment of the present invention, when the second-stranded DNA is synthesized, a mixture of 25 mM dNTPs and dUTP is used, wherein the molar ratio of dUTP to dTTP is 4:1.

In the step, between "synthesizing the second-stranded DNA" and "repairing the tail end of dsDNA, between "repairing the tail end of dsDNA" and "adding 'A' to the DNA with the tail end repaired", and after "ligating an adapter", a DNA purification step can also be included. The purification method can be magnetic bead purification. The specific method of magnetic bead purification can be carried out according to the following steps: uniformly mixing and balancing AMPure XP magnetic beads (XP magnetic beads for short) in advance at room temperature for 30 minutes, then adding the XP magnetic beads into the eluent, and uniformly mixing the sample gently; incubating at room temperature for 5 minutes, transferring to the magnetic stand and stewing for 5 minutes, removing the supernatant, and washing the magnetic bead twice with the fresh 80% (v/v) ethanol solution; drying the magnetic beads on the magnetic stand for 2 minutes, adding the TE buffer to resuspend the magnetic beads, and pipetting up and down for 50 times; and incubating at room temperature for 5 minutes, then stewing the magnetic beads on the magnetic stand for 5 minutes, and collecting the supernatant, that is, the purified DNA product. Wherein, the DNA purification step (such as magnetic bead purification) after the "ligating an adapter" can be twice.

In the specific embodiment of the present invention, forward and reverse primers used in the PCR amplification in this step are the paired primer composed of two single-stranded DNAs shown in SEQ ID No. 1 and SEQ ID No. 2. Specifically, the reaction system of the PCR amplification performed in this step is as follows: 15.7 μl of supernatant (the supernatant obtained the step of purifying the DNA with magnetic beads after "ligating an adapter"), 2.5 μl of 10×Pfx buffer (Invitrogen), 1 μl of 10 μM forward primer and 1 μl of 10 μM reverse primer (SEQ ID No. 1 and SEQ ID No. 2), 1 μl of 50 mM MgSO$_4$ solution, 0.4 μl of 25 mM dNTP, 0.4 μl of Pfx enzyme (Invitrogen), and 3 μl of USER enzyme (NEB). The specific reaction procedures of the PCR amplification are as follows: incubating at 37° C. for 15 minutes; incubating at 94° C. for 2 minutes; denaturing at 94° C. for 15 seconds, annealing at 62° C. for 30 seconds, extending at 72° C. for 30 seconds, and the reaction is carried out for 12 cycles; and incubating at 72° C. for 10 minutes.

In the step (6) of the method, the high-throughput sequencing can use the Illumina HiSeq X Ten sequencer to sequence the library obtained in the step (5), and can perform PE150 paired-end sequencing.

In the method, the maximum starting amount of the cells is $1 \times 10^7$ cells.

Further, the cell can be the animal cell (such as a human-derived cell), and the tissue may be the animal tissue. In the specific embodiment of the present invention, the cell is specifically HeLa cell.

In the second aspect, the present invention claims a library construction method.

The library construction method as claimed in the present invention includes the steps (1) to (5) of the method described in the first aspect above.

In the third aspect, the present invention claims an application of the library constructed by using the method described in the second aspect for capturing RNA higher-order structure in situ and/or identifying the in situ RNA-RNA interaction.

In a fourth aspect, the present invention further claims any of the following applications:

(A1) an application of the method described in the first aspect above for identifying lncRNA targets in living cells.

(A2) an application of pCp-biotin for identifying RNA-RNA close-range interactions; wherein the close range can be within 50 angstroms.

(A3) an application of pCp-biotin in RNA in situ proximal ligation; wherein the proximal distance can be within 50 angstroms.

(A4) an application of pCp-biotin in chimeric RNA enrichment.

In the fifth aspect, the present invention further claims any one of the following:

(B1) the detergent, which is the Permeabilization solution described above.

(B2) an auxiliary use of the detergent described in the step (B1) in the membrane permeabilization of cells.

(B3) an application of the MNase, the alkaline phosphatase and/or the T4 Polynucleotide Kinase (T4 PNK) in the in situ ligation of RNA (such as in situ proximal ligation).

(B4) use of the proteinase K and heating for extracting the RNA from the formaldehyde-fixed cell sample or tissue sample. Wherein, the heating refers to the reaction at 37° C. for 60 minutes and the reaction at 56° C. for 15 minutes.

In the present invention, the in situ ligation is in situ ligation under non-denaturing conditions.

DETAILED DESCRIPTION OF THE EMBODIMENTS

Figure 1:
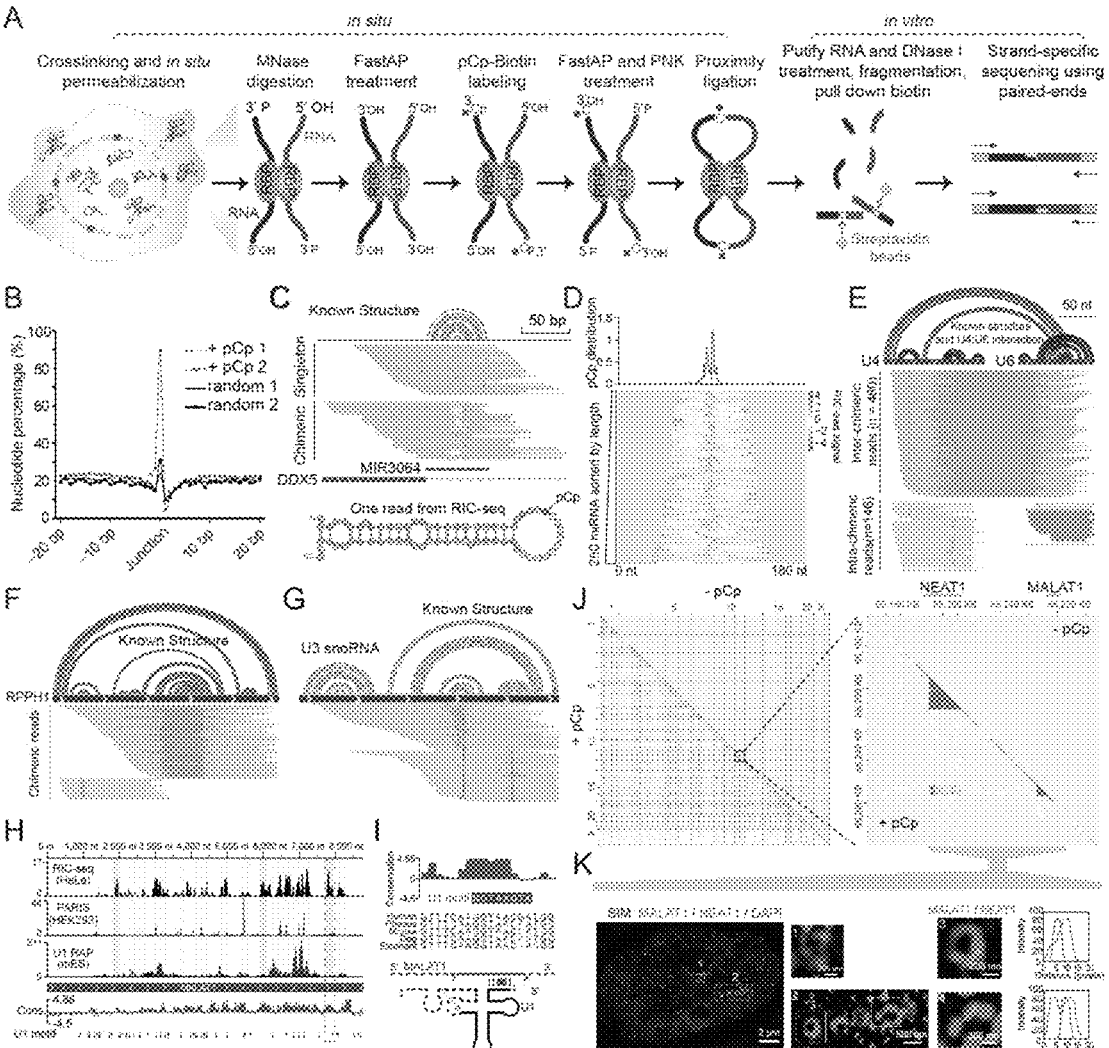
FIG. 1. Overview and evaluation of RIC-seq. (A) Schematic diagram of the RIC-seq process. The in situ part includes formaldehyde crosslinking, permeabilization, RNA digestion, pCp-biotin labeling and proximity ligation. For the in vitro part, chimeric RNAs were enriched and converted into libraries for paired-end sequencing. RBP stands for RNA-bound proteins. (B) The base content surrounding the junction of chimeric reads. (C) Comparison of known structures (blue arcs) of miR3064 to RIC-seq chimeric reads (gray boxes). The light blue lines between chimeric reads represent gaps. The stem-loop structural model of a single RIC-seq read is shown at the bottom, and the pCp insertion is marked in red. (D) pCp is enriched in the apical loop of pre-miRNAs. (E-G) RIC-seq recapitulates known structures and interactions of U4, U6, RPPH1 and U3 snoRNA. (H) RIC-seq identifies U1 binding sites in MALAT1. Pink shaded regions are shared between RIC-seq datasets and PARIS or RAP data. Blue shaded peaks are detected only by RIC-seq. The dashed-line boxed region is shown in (I). (I) Novel U1 interacting sites in MALAT1 are conserved and proved by chimeric clusters (gray arrowheads). U1 motif shown in purple. (J) RNA map showing RNARNA interactions across all chromosomes. Lower left, +pCp samples. Upper right, −pCp samples. The NEAT1 and MALAT1 interactions are magnified and shown on the right. (K) SIM analysis revealed colocalization of MALAT1 and the NEAT1 5' end. The regions marked Box 1 and Box 2 are magnified in the middle panel. The direct overlapping loci in Box 3 and Box 4 are shown in yellow.

The following embodiments facilitate a better understanding of the present invention, but do not limit the present invention. The experimental methods in the following embodiments, unless otherwise specified, are all conventional methods. The test materials used in the following embodiments, unless otherwise specified, are all purchased from conventional biochemical reagent stores.

The formulations of solutions used in the following embodiments are as follows:

PBS buffer (pH 7.4): the solvent is water, and the solute and concentration are as follows: 137 mmol/L of NaCl, 2.7 mmol/L of KCl, 10 mmol/L of $Na_2HPO_4$, and 2 mmol/L of $KH_2PO_4$.

1×PNK solution: the solvent is 50 mM Tris-HCl buffer with pH 7.4, and the solute and concentration are as follows: 10 mM of $MgCl_2$, 0.1 mg/ml of BSA, and 0.2% (v/v) NP-40.

1×PNK+EGTA solution: the solvent is 50 mM Tris-HCl buffer with pH 7.4, and the solute and concentration are as follows: 20 mM of EGTA, and 0.5% (v/v) NP-40.

High-salt solution: the solvent is a 5×PBS (no $Mg^{2+}$, $Ca^{2+}$), and the solute and concentration are as follows: 0.5% (v/v) NP-40. Wherein, the 5×PBS (no $Mg^{2+}$, $Ca^{2+}$) is the 5×PBS buffer (pH 7.4): 685 mmol/L of NaCl, 13.5 mmol/L of KCl, 50 mmol/L of $Na_2HPO_4$, and 10 mmol/L of $KH_2PO_4$.

Permeabilization solution: 10 mM of Tris-HCl (pH 7.5), 10 mM of NaCl, 0.5% (v/v) NP-40, 0.3% (v/v) Triton X-100, 0.1% (v/v) Tween 20, 1×protease inhibitors (Sigma, catalog number: P8340-5ML, the specific components include AEBSF, Aprotinin, Bestatin hydrochloride, E-64, Leupeptin hemisulfate salt and Pepstatin A) and 2 U/ml of SUPERase.In™ RNase Inhibitor (Thermo Fisher, catalog number: AM2694).

1×MN reaction solution: the solvent is 50 mM Tris-HCl buffer with pH 8.0, and the solute and concentration are as follows: 5 mM of $CaCl_2$).

Proteinase K solution: the solvent is 10 mM of Tris-HCl buffer with pH 7.5, and the solute and concentration are as follows: 10 mM of EDTA, and 0.5% (w/v) SDS.

5×hybridization solution: 1M of NaCl, and 500 mM of Tris-HCl (pH 7.4).

Solution A: 0.1 M of NaOH, and 0.05 M of NaCl.

Solution B: 0.1 M of NaCl.

2×TWB solution: 10 mM of Tris-HCl (pH 7.5), 1 mM of EDTA, 2 M of NaCl, and 0.02% (v/v) Tween 20.

PK solution: 100 mM of NaCl, 10 mM of Tris-HCl (pH 7.0), 1 mM of EDTA, and 0.5% (w/v) SDS.

TE buffer: 10 mM of Tris-HCl (pH 8.0), and 1 mM of EDTA.

Embodiment 1. Preparation Method of a RIC-Seq Library

The construction process of the RIC-seq library of the present invention is shown in FIG. 1A. The construction process includes cell culture, formaldehyde cross-linking, cell membrane and nuclear membrane permeabilization, MNase enzyme treatment, hydroxylation treatment of the 3' end of RNA, pCp-biotin ligation, hydroxylation treatment of the 3' end of the RNA, phosphorylation treatment of the 5' end, proximal ligation, total RNA extraction, removal of genomic DNA by DNase I, removal of ribosome RNA, RNA fragmentation, C1 magnetic bead enrichment and elution of the enriched RNA, cDNA first-stranded synthesis, second-stranded synthesis of DNA, tail end repair, "A" addition, adapter ligation, PCR amplification and other steps. The specific steps are as follows:

1. Taking cells in a 15 cm dish with a density of about 80-90%, discarding the culture medium, adding 10 ml of precooling PBS (pH 7.4) to wash the cells, discarding the PBS, and repeating this step 3 times to obtain washed cells.

2. After completing the step 1, adding 10 ml of 1% (v/v) formaldehyde solution (the solvent is PBS solution) into the washed cells obtained in the step 1, and incubating at room temperature for 10 minutes. Then adding a glycine solution (the final concentration is 0.125 mol/L, and the solvent is DEPC water) to terminate the reaction, and incubating at room temperature for 10 minutes to obtain formaldehyde cross-linked and terminated cells.

3. After completing the step 2, adding 10 ml of precooling PBS (pH 7.4) into the formaldehyde cross-linked and terminated cells obtained in the step 2, performing washing for 3 times, scraping the cells with a cell lifter and transferring the cells into a 50 ml centrifuge tube, performing centrifugation at 2500 rpm for 10 minutes at 4° C., discarding the supernatant, adding 2 ml of precooling PBS (pH 7.4) to resuspend the cell pellet, transferring the cell suspension into two 1.5 ml eppendorf centrifuge tubes, wherein 1 ml of cell suspension is transferred into each eppendorf centrifuge tube, performing centrifugation at 2500 rpm for 10 minutes at 4° C., discarding the supernatant, and continuing the next step or storing the cell pellet in a refrigerator at −80° C.

4. After completing the step 3, adding 1 ml of Permeabilization buffer into the cell pellet obtained in the step 3, incubating on ice for 15 minutes, and uniformly mixing the solution every 2 minutes. performing centrifugation at 3500 rpm for 5 minutes at 4° C., discarding the supernatant, adding 600 μl of 1×PNK buffer to resuspend the cell pellet, performing uniform mixing for 5 minutes at 4° C. by rotating (20 rpm), performing centrifugation at 3500 rpm for 5 minutes at 4° C., discarding the supernatant, and repeating this step twice.

5. After completing the step 4, adding 200 μl of MNase (Thermo Fisher with the catalog number of EN0181) diluted at a volume ratio of 1:10000 into the cell pellet obtained in the step 4 with 1×MN buffer (wherein the concentration of the MNase enzyme is 0.03 U/μl) to resuspend the cell pellet, Incubate the suspension in the ThermoMixer at 37° C. for 10 minutes with intermittent mixing at 1000 rpm every 2 min for 15 sec. After the reaction is completed, centrifuging the tube at 3500 rpm for 5 minutes at 4° C., discarding the supernatant, adding 600 μl of 1×PNK+EGTA buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 μl of 1×PNK buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once.

6. After completing the step 5, adding 10 μl of 10×FastAP buffer (the product of the Thermo Fisher company), 10 μl of Fast Alkaline Phosphatase (the product of the Thermo Fisher company with the catalog number of EF0651; and the final concentration in the reaction system is 0.1 U/μl), and 80 μl of DEPC water into the cell pellet obtained in the step 5 to resuspend the cell pellet, incubating in the ThermoMixer at 37° C. for 10 minutes with intermittent mixing at 1000 rpm every 3 min for 15 sec. After the reaction is completed, centrifuging the tube at 3500 rpm for 5 minutes at 4° C., discarding the supernatant, adding 600 μl of 1×PNK+EGTA buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 μl of high-salt buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 μl of 1×PNK buffer (compared with the previous formula, the content of NP-40 is adjusted to 0.05% (v/v), while the other ingredients and contents remain unchanged) to resuspend the cell pellet, performing uniform mixing for 5 minutes at 4° C. by rotating (20 rpm), centrifuging the tube at 3500 rpm for 5 minutes at 4° C., discarding the supernatant, and repeating this step once.

7. After completing the step 6, adding 10 μl of 10×RNA ligase reaction buffer (the product of the Thermo Fisher company), 6 μl of RNase inhibitor, 4 μl of Biotinylated Cytidine (Bis) phosphate (i.e., pCp-biotin, the product of the Thermo Fisher company with the catalog number of 20160) (1 mM), 10 μl of T4 RNA ligase (the product of the Thermo Fisher company with the catalog number of EL0021; and the final concentration in the reaction system is 1 U/μl), 20 μl of DEPC water and 50 μl of 30% PEG into the cell pellet obtained in the step 6 to resuspend the cell pellet, incubating at 16° C. in the ThermoMixer for overnight with intermittent mixing at 1000 rpm every 3 min for 15 sec. After the reaction is completed, performing centrifugation at 4° C. and 3500 rpm for 5 minutes, discarding the supernatant, adding 600 μl of 1×PNK solution to resuspend the cell pellet, performing uniform mixing for 5 minutes at 4° C. by rotating (20 rpm), centrifuging the tube at 3500 rpm for 5 minutes at 4° C., discarding the supernatant, and repeating this step twice.

8. After completing the step 7, adding 10 μl of 10×FastAP buffer (the product of the Thermo Fisher company), 10 μl of Fast Alkaline Phosphatase (the product of the Thermo Fisher company with the catalog number of EF0651; and the final concentration in the reaction system is 0.1 U/μl), and 80 μl of DEPC water into the cell pellet obtained in the step 7 to resuspend the cell pellet, incubating in the ThermoMixer at 37° C. for 10 minutes with intermittent mixing at 1000 rpm every 3 min for 15 sec. After the reaction is completed, centrifuging the tube at 3500 rpm for 5 minutes at 4° C., discarding the supernatant, adding 600 μl of 1×PNK+EGTA buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 μl of high-salt buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 μl of 1×PNK buffer (compared with the previous formula, the content of NP-40 is adjusted to 0.05% (v/v), while the other ingredients and contents remain unchanged) to resuspend the cell pellet, performing uniform mixing for 5 minutes at 4° C. by rotating (20 rpm), centrifuging the tube at 3500 rpm for 5 minutes at 4° C., discarding the supernatant, and repeating this step twice.

9. After completing the step 8, adding 10 μl of 10×PNK buffer (the product of the Thermo Fisher company), 15 μl of 10 mM ATP, 10 μl of T4 PNK (the product of the Thermo Fisher company with the catalog number of EK0032; and the final concentration in the reaction system is 1 U/μl), and 65 μl of DEPC water into the cell pellet obtained in the step 8 to resuspend the cell pellet, incubating at 37° C. for 45 minutes in the ThermoMixer with intermittent mixing at 1000 rpm every 3 min for 15 sec. After the reaction is completed, centrifuging the tube at 3500 rpm for 5 minutes at 4° C., discarding the supernatant, adding 600 μl of 1×PNK+EGTA buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step once. Adding 600 µl of 1×PNK buffer (compared with the previous formula, the content of NP-40 is adjusted to 0.05% (v/v), while the other ingredients and contents remain unchanged) to resuspend the cell pellet, performing uniform mixing for 5 minutes at 4° C. by rotating (20 rpm), centrifuging the tube at 3500 rpm for 5 minutes at 4° C., discarding the supernatant, and repeating this step once.

10. After completing the step 9, adding 20 µl of 10×RNA ligase reaction buffer (the product of the Thermo Fisher company), 8 µl of RNase inhibitor, 10 µl of T4 RNA ligase (the product of the Thermo Fisher company with the catalog number of EL0021; and the final concentration in the reaction system is 0.5 U/µl), 20 µl of BSA (1 mg/ml) and 142 µl of DEPC water into the cell pellet obtained in the step 9 to resuspend the cell pellet, incubating in the ThermoMixer at 16° C. for overnight with intermittent mixing at 1000 rpm every 3 min for 15 sec. After the reaction is completed, centrifuging the tube at 3500 rpm for 5 minutes at 4° C., discarding the supernatant, adding 600 µl of 1×PNK buffer to resuspend the cell pellet, performing uniform mixing for 5 minutes at 4° C. by rotating (20 rpm), centrifuging the tube at 3500 rpm for 5 minutes at 4° C., discarding the supernatant, and repeating this step twice.

11. After completing the step 10, adding 200 µl of Proteinase K buffer and 50 µl of proteinase K (the product of the Takara company with the catalog number of 9034; and the final concentration in the reaction system is 0.12 U/µl) into the cell pellet obtained in the step 10, performing uniform mixing, incubating in the ThermoMixer at 37° C. for 60 minutes and then 56° C. for 15 minutes. After the reaction is completed, let the sample cool to room temperature, and then adding 750 µl of Trizol LS (the product of the Thermo Fisher company with the catalog number of 10296028), incubating at room temperature for 5 minutes after mixing by pipetting up and down, adding 220 µl of chloroform, shaking vigorously for 15 seconds, and incubating at room temperature for 3 minutes. Centrifuge the tube at 13000 rpm for 15 minutes at 4° C., transferring the supernatant into a 1.5 ml eppendorf centrifuge tube, adding 500 µl of isopropanol and 1 µl of glycoblue (the concentration is 15 µg/µl), mixing by pipetting up and down, and placing the centrifuge tube in a −20° C. refrigerator to precipitate for overnight.

12. After completing the step 11, centrifuging the sample obtained in the step 11 at 13000 rpm for 20 minutes at 4° C., discarding the supernatant, adding 500 µl of 75% ethanol, washing the pellet, centrifuging the tube at 13000 rpm for 5 minutes at 4° C., repeating this step once, drying the pellet, adding 20 µl of DEPC water to dissolve the pellet, taking 1 µl of sample and quantifying with NanoDrop.

13. After completing the step 12, taking out 20 µg of total RNA from the sample obtained in the step 12, adding 10 µl of 10×RQ1 DNase I buffer (the product of the Promega company), 3 µl of RNAsin (the product of the Thermo Fisher company with the catalog number of E00381) and 5 µl of DNase I (the product of the Promega company with the catalog number of M6101), making up to 100 µl with DEPC water, incubating at 37° C. for 20 minutes in ThermoMixer, after the reaction is completed, adding 100 µl of DEPC water, then adding 200 µl of acid-phenol:chloroform (pH 4.5), mixing by pipetting up and down, incubating at room temperature for 3 minutes, centrifuging the tube at 13000 rpm for 15 minutes at 4° C., transferring the supernatant into a 1.5 ml eppendorf centrifuge tube, adding 20 µl of 3M sodium acetate (pH 5.5), 1 µl of glycoblue and 500 µl of 100% ethanol, mixing by pipetting up and down, and placing the centrifuge tube in the −20° C. refrigerator to precipitate for overnight.

14. After completing the step 13, centrifuging the sample obtained in the step 13 at 13000 rpm for 20 minutes at 4° C., discarding the supernatant, adding 500 µl of 75% ethanol, washing the pellet, centrifuging the tube at 13000 rpm for 5 minutes at 4° C., repeating this step once, drying the pellet, adding 6 µl of DEPC water to dissolve the pellet, and transferring the sample into the PCR tube.

15. After completing the step 14, adding 10 µl of rRNA probe mix (2 µg/l) (the design and synthesis of the probe sequence refer to published reference (Adiconis, X., Borges-Rivera, D., Satija, R., DeLuca, DS, Busby, M A, Berlin, A M, Sivachenko, A., Thompson, D A, Wysoker, A., Fennell, T., et al. (2013). Comparative analysis of RN A sequencing methods for degraded or low-input samples. Nature methods 10, 623-629.), and 4 µl of 5× hybridization buffer into the sample obtained in the step 14, mixing by pipetting up and down, placing the PCR tube in a PCR thermal cycler, setting the reaction program as follows: incubating at 95° C. for 2 minutes, cooling to 22° C. at a speed of 0.1° C./s, incubating at 22° C. for 5 minutes, and immediately putting the sample on ice after the reaction is completed.

16. After completing the step 15, adding 3 µl of 10×RNase H buffer (the product of the Thermo Fisher company), 5 µl of RNase H (the product of the Thermo Fisher company with the catalog number of EN0202) (25U) and 2 µl of DEPC water into the sample obtained in the step 15, mixing by pipetting up and down, placing the sample in the PCR thermal cycler, and setting the reaction program as follows: incubating at 37° C. for 30 minutes, and immediately putting the sample on ice after the reaction is completed.

17. After completing the step 16, adding 4 µl of 10×TURBO buffer (the product of the Thermo Fisher company), 5 µl of TURBO DNase (the product of the Thermo Fisher company with the catalog number of AM2238; and the final concentration in the reaction system is 0.25 U/µl), and 1 µl of DEPC water into the sample obtained in the step 16, mixing by pipetting up and down, placing the sample in the PCR thermal cycler, and setting the reaction program as follows: incubating at 37° C. for 30 minutes, and immediately putting the sample on ice after the reaction is completed.

18. After completing the step 17, transferring the sample obtained in the step 17 into a 1.5 ml eppendorf centrifuge tube, adding 160 µl of DEPC water, adding 200 µl of acid-phenol:chloroform (pH 4.5), mixing by pipetting up and down, incubating at room temperature for 3 minutes, centrifuging the tube at 13000 rpm for 15 minutes at 4° C., transferring the supernatant into a 1.5 ml eppendorf centrifuge tube, adding 20 µl of 3M sodium acetate (pH 5.5), 1 µl of glycoblue and 500 µl of 100% ethanol, mixing by pipetting up and down, and placing the centrifuge tube in the −20° C. refrigerator to precipitate for overnight.

19. After completing the step 18, centrifuging the sample obtained in the step 18 at 13000 rpm for 20 minutes at 4° C., discarding the supernatant, adding 500 µl of 75% ethanol, washing the pellet, performing centrifugation at 4° C. and 13000 rpm for 5 minutes, repeating this step once, drying the precipitate naturally, adding 16 µl of DEPC water to dissolve the precipitate, transferring the sample into a PCR tube, adding 4 µl of 5× first-strand buffer (the product of the Thermo Fisher company with the catalog number of 18064-014), performing uniform mixing, placing the sample in the PCR thermal cycler, incubating at 94° C. for 5 minutes, and immediately putting the sample on ice after the reaction is completed.

20. Taking a 1.5 ml centrifuge tube, adding 20 μl of C1 magnetic beads, placing the centrifuge tube on a magnetic stand, removing the supernatant after the solution is clear, adding 20 μl of solution A, resuspending the magnetic beads, incubating at room temperature for 2 minutes, putting the centrifuge tube on the magnetic stand, removing the supernatant after the solution is clear, repeating this step once, adding 20 μl of solution B, resuspending the magnetic beads, putting the centrifuge tube on the magnetic stand, removing the supernatant after the solution is clear, adding 32 μl of yeast RNA (the product of the Roche company with the catalog number of 10109223001) (50 kg), 68 μl of DEPC water and 100 μl of 2×TWB solution, resuspending the magnetic beads, putting the centrifuge tube on a rotary mixer, uniformly mixing for 1 hour by rotating, then putting the centrifuge tube on the magnetic stand, removing the supernatant after the solution is clear, adding 500 μl of 1×TWB solution, resuspending the magnetic beads, putting the centrifuge tube on the magnetic stand, removing the supernatant after the solution is clear, and repeating this step twice.

21. Taking the sample obtained in the step 19, adding 30 μl of DEPC water and 50 μl of 2×TWB buffer, adding a total of 100 μl sample into the blocked magnetic beads, performing uniform mixing for 30 minutes by rotating at room temperature, putting the centrifuge tube on the magnetic stand, removing the supernatant after the solution is clear, performing washing for 4 times with 500 μl of 1×TWB buffer of each time.

22. After completing the step 21, adding 100 μl of PK buffer into the washed magnetic beads obtained in the step 21, performing uniform mixing, incubating the sample at 95° C. for 10 minutes at 1000 rpm in the ThermoMixer, putting the centrifuge tube on the magnetic stand, transferring the supernatant into a new 1.5 ml centrifuge tube after the solution is clear, adding 100 μl of PK buffer into the original tube, performing uniform mixing, incubating the sample at 95° C. for 10 minutes at 1000 rpm in the ThermoMixer, putting the centrifuge tube on the magnetic stand, transferring the supernatant into the same 1.5 ml centrifuge tube after the solution is clear, adding 100 μl of PK buffer into the original tube, performing uniform mixing, putting the centrifuge tube on the magnetic stand, transferring the supernatant into the same 1.5 ml centrifuge tube after the solution is clear. For 300 μl of eluent in total, adding 300 μl of acid-phenol:chloroform (pH 4.5), performing uniform mixing, incubating at room temperature for 3 minutes, centrifuging the tube at 13000 rpm for 15 minutes at 4° C., transferring the supernatant into a new 1.5 ml centrifuge tube, adding 18 μl of 5M NaCl, mixing by pipetting up and down, adding 1 μl of glycoblue and 900 μl of 100% ethanol, mixing by pipetting up and down, and placing the centrifuge tube in the −20° C. refrigerator to precipitate for overnight.

23. After completing the step 22, centrifuging the sample obtained in the step 22 at 13000 rpm for 20 minutes at 4° C., discarding the supernatant, adding 500 μl of 75% ethanol, washing the pellet, centrifuging the tube at 13000 rpm for 5 minutes at 4° C., repeating this step once, drying the precipitate naturally, adding 10 μl of DEPC water to dissolve the pellet, transferring the sample into a PCR tube, adding 0.5 μl of N6 primer (the sequence is NNNNNN, wherein N represents A or T or C or G) (0.1 g/l), mixing by pipetting up and down, placing the PCR tube in the PCR thermal cycler, incubating at 65° C. for 5 minutes, and immediately putting the sample on ice after the reaction is completed.

24. After completing the step 23, adding 3 μl of 5×first-strand buffer (the product of the Thermo Fisher company with the catalog number of 18064-014), 1 μl of dNTP mix (10 mM), 0.5 μl of 100 mM DTT, 0.5 μl of RNase Inhibitor (40 U/μl), and 0.5 μl of Superscript II (the product of the Thermo Fisher company with the catalog number of 18064-014) (200 U/μl) into the sample obtained in the step 23, mixing by pipetting up and down, putting the PCR tube in the PCR thermal cycler, and setting the program as follows: incubating at 25° C. for 10 minutes, incubating at 42° C. for 40 minutes, and incubating at 70° C. for 15 minutes. After the reaction is completed, put the sample on ice.

25. After completing the step 24, transferring the sample obtained in the step 24 into a new 1.5 ml centrifuge tube, adding 10 μl of 5× Second-strand buffer (the product of the Thermo Fisher company with the catalog number of 10812-014), 0.8 μl of dNTP (dUTP) (25 mM) (i.e., a mixture of 25 mM dNTPs and dUTP, wherein the molar ratio of dUTP to dTTP is 4:1), 0.2 μl of RNase H (the product of the Thermo Fisher company with the catalog number of EN0202) (5 U/μl), and 2.5 μl of DNA Pol I (the product of the Enzymatics company with the catalog number of P705-500) (10 U/μl), putting the centrifuge tube in the ThermoMixer, and setting the reaction program as: 16° C. for 2 hours with intermittent mixing at 300 rpm every 3 min for 15 sec.

26. After completing the step 25, uniformly mixing and balancing XP magnetic beads in advance at room temperature for 30 minutes, then adding 90 μl of (1.8×) XP magnetic beads into the reaction solution obtained in the step 25, and performing gentle mixing. Incubating at room temperature for 5 minutes, transferring the solution to the magnetic stand and stewing for 5 minutes, removing the supernatant, and washing the magnetic beads twice with 200 μl of fresh 80% ethanol solution each time. Placing the magnetic beads on the magnetic stand to dry for 2 minutes, adding 43 μl of TE buffer to resuspend the magnetic beads, and mixing by pipetting up and down for 50 times. Incubating at room temperature for 5 minutes, then putting the magnetic beads on the magnetic stand and stewing for 5 minutes, and transferring the supernatant (42 μl) into the 1.5 ml centrifuge tube.

27. After completing the step 26, adding 5 μl of 10×PNK solution (T4 PNK supporting reaction solution), 0.4 μl of dNTPs (25 mM), 1.2 μl of T4 DNA polymerase (the product of the Enzymatics company with the catalog number of P7080L), (3 U/μl), 0.2 μl of Klenow fragment (the product of the Enzymatics company with the catalog number of P7060L) (5 U/μl), and 1.2 μl of T4 PNK (the product of the Enzymatics company with the catalog number of Y9040L) (10 U/μl) into the sample obtained in the step 26, mixing by pipetting up and down, and incubating for 30 minutes at 20° C. in the ThermoMixer. After the reaction is completed, adding 90 μl of XP magnetic beads for purification, the specific steps are the same as the step 26, finally, using 20.5 μl of TE buffer for elution, transferring the supernatant (19.7 μl) into the new 1.5 ml centrifuge tube.

28. After completing the step 27, adding 2.3 μl of 10×blue buffer (the product of the Enzymatics company with the catalog number of B0110L), 0.5 μl of dATP (5 mM) and 0.5 μl of Klenow exo-(3' to 5' exo minus) (the product of the Enzymatics company with the catalog number of P7010-LC-L) (5 U/μl), mixing by pipetting up and down, putting the centrifuge tube, incubating for 30 minutes at 37° C. in the ThermoMixer.

29. After completing the step 28, adding 1.4 of μl 2×Rapid ligation buffer (the product of the Enzymatics company with the catalog number of B1010L), 0.1 μl of mM ATP, 1 μl of Adapter (PEI Adapter oligo A:/5Phos/GATCG-GAAGAGCACACGTCT (5Phos: 5' phosphorylation), PEI Adapter oligo B: ACACTCTTTCCCTAC ACGACGCTCTTCCGATCT, the adapter in the reaction is formed by annealing two oligos) (2 μM), and 1 μl of T4 DNA ligase (Rapid) (the product of the Enzymatics company with the catalog number of L6030-HC-L) (600 U/μl) into the sample obtained in the step 28, mixing by pipetting up and down, incubating for 15 minutes at 20° C. in the ThermoMixer. After the reaction is completed, adding 47.7 μl of XP magnetic beads for purification, the specific steps are the same as the step 26, finally, using 26 μl of TE buffer for elution, transferring the supernatant (25 μl) into the new 1.5 ml centrifuge tube. Adding 45 μl of XP magnetic beads for secondary purification, the specific steps are the same as the step 26, finally, using 16.5 μl of TE buffer for elution, transferring the supernatant (15.7 μl) into the PCR tube.

30. After completing the step 29, using the supernatant obtained in the step 29 as the template to perform PCR reaction in the PCR tube to obtain the PCR reaction solution (25 μl).

The PCR reaction system is 25 μl: 15.7 μl of supernatant, 2.5 μl of 10×Pfx buffer (Invitrogen), 1 μl of 10 μM forward and 1 μl of 10 μM reverse primers, 1 μl of 50 mM MgSO₄ solution, 0.4 μl of 25 mM dNTP, 0.4 μl of Pfx Enzyme (Invitrogen), and 3 μl of USER enzyme (NEB).

The PCR reaction procedure is as follows: incubating at 37° C. for 15 minutes; incubating at 94° C. for 2 minutes; denaturing at 94° C. for 15 seconds, annealing at 62° C. for 30 seconds, extending at 72° C. for 30 seconds, and the reaction is carried out for 12 cycles; and incubating at 72° C. for 10 minutes.

31. After completing the step 30, performing electrophoresis on the PCR reaction solution obtained in the step 30 by using 2% agarose gel, recovering the product within a range of 200-450 bp by using the Qiagen MinElute Gel Extraction Kit according to the manufacture's instruction, and finally using 16 μl of TE buffer for elution to obtain PCR eluate.

32. After completing the step 31, taking 1 μl of the PCR eluate obtained in the step 31 and quantifying it by using Qubit 3.0. The qualified sample is used for sequencing analysis.

Embodiment 2. Application of the Preparation Method of the RIC-Seq Library

1. Culture of HeLa Cells and *Drosophila* S2 Cell Samples

The HeLa cells cultured in a laboratory are used as samples, the initial amount of the cell samples is 1×10⁷ cells, and the *Drosophila* S2 cells are used as spike-in to evaluate the specificity of the proximal ligation.

2. Preparation of the RIC-Seq Library

The RIC-seq library is constructed according to the method in Embodiment 1 based on the cell sample in the step 1. The forward and reverse primers in the step 30 are as follows (NNNNNNN is a library Index sequence) Primer1.0

(SEQ ID No. 1)
5'-AATGATACGGCGACCACCGAGATCTACACTCTTTCCCTACACGACG

CTCTTCCGATCT-3';

Index Primer (SEQ ID No. 2)
5'-CAAGCAGAAGACGGCATACGAGATANNNNNNNNGTGACTGGAGTTCA

GACGTGTGCTCTTCCGATCT-3'.

Wherein, N represents A or T or C or G.

3. Sequencing

PE150 paired-end sequencing is performed on the RIC-seq library constructed in the step 2 by using an Illumina HiSeq X Ten sequencer.

4. Data Analysis and Results

1. Data Analysis Method

Figure 2:
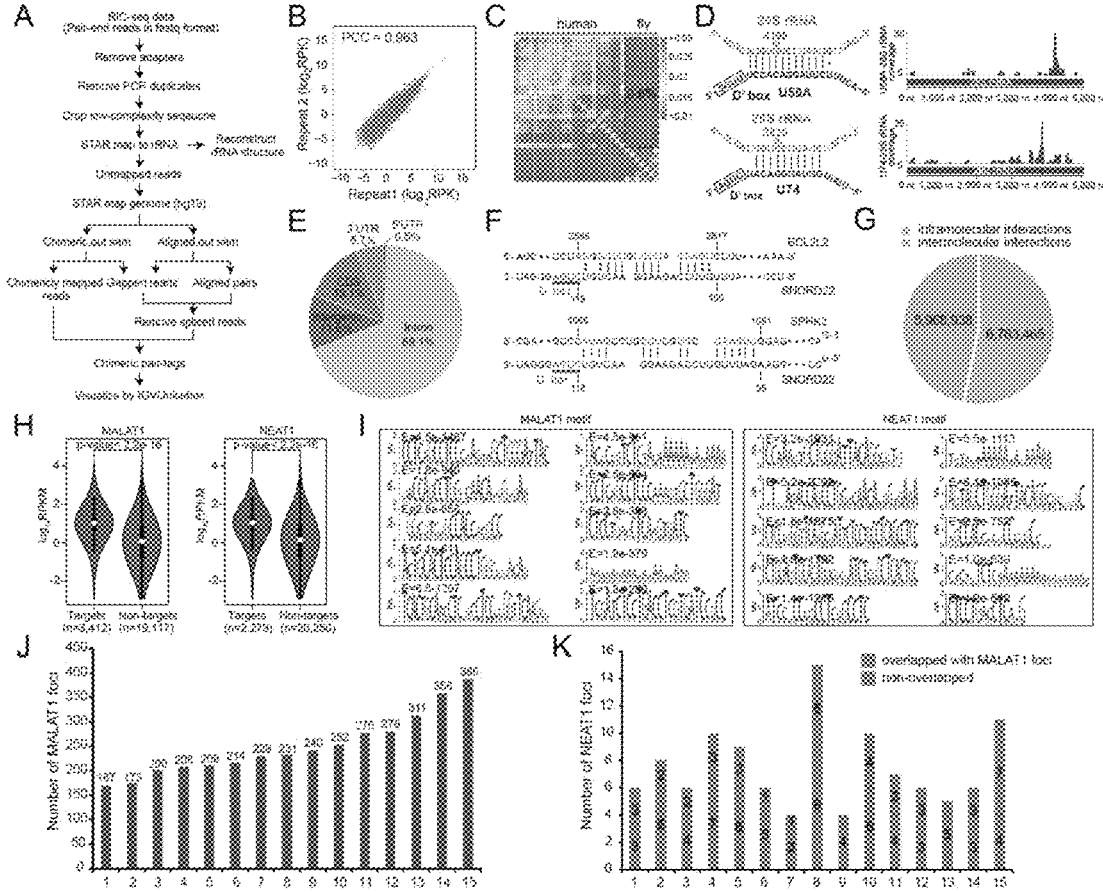
FIG. 2. The mapping pipeline and reproducibility of RIC-seq. (A) The mapping pipeline for RIC-seq data. PCR duplicates, adapters and reads containing polyN were first removed. After filtering, the paired reads were mapped separately to the hg19 reference genome using the STAR program. (B) RIC-seq replicates are highly correlated. (C) The global false positive rate of RIC-seq is 0.6% (dashed-line boxed region) by a cell mixing strategy. (D) RIC-seq recapitulates snoRNA interacting sites in 28S rRNA. The red arrow indicates known modification sites. The boxed region represents the D' box. (E) The genomic distribution of snoRNA interacting sites detected by RIC-seq. (F) The SNORD22 interacting sites in SPHK2 and BCL2L2 genes. The D-box is shown in blue. (G) The pie chart of intramolecular and intermolecular RNA-RNA interactions. (H) The violin plot shows the expression levels of MALAT1- and NEAT1-targeting genes. The P-value was calculated by a two-tailed Student's t-test. (I) The enriched motifs among MALAT1 or NEAT1 chimeric targets. (J) Summary of MALAT1 loci in 15 cells. (K) Summary of NEAT1 loci and their overlap with MALAT1 in 15 cells by smFISH. Blue bars represent the direct overlap between NEAT1 and MALAT1 loci.

The data analysis process is shown as 'A' panel in FIG. 2. First, using the Trimmomatic (0.36) software to filter out adapter sequences and low-quality sequencing fragments in the RIC-seq raw sequencing data, then using Cutadapt (v1.15) to trim low-complexity sequences such as polyA after further removing duplicated fragments, then using STAR (2.5.2b) to align high-quality data to the human reference genome (hg19 version), and finally screening sequencing fragments from RNA ligation products (defined as chimeric reads) from the alignment results. By comparing the number of chimeric reads of each gene, the Pearson correlation coefficient is calculated to evaluate the reproducibility of the experiment. The IGVtools and Juicebox are used to visualize RIC-seq data.

2. Data Analysis Results

In order to capture the protein-mediated RNA proximal ligation, we invented the RIC-seq method (RNA In situ Conformation Sequencing). The specific process is shown as 'A' panel in FIG. 1. First, the cells are treated with formaldehyde to fix the protein-RNA, protein-DNA and protein-protein interactions, so that different RNA fragments that are close in space are fixed. Secondly, the cell membrane and the nuclear membrane of the fixed cells are permeabilized by using multiple groups of detergents, and treated with MNase to remove the free RNAs that are not protected by protein. After treatment with MNase, the 3' end of the RNA is the phosphate group, and the 5' end is the hydroxyl group (FIG. 1A). In order to label pCp-biotin, we use alkaline phosphatase to convert the phosphate group at the 3' end into hydroxyl group, and then use T4 RNA ligase to label the pCp-biotin to the 3' end of the RNA. Immediately afterwards, the samples are treated with the alkaline phosphatase and the T4 PNK enzyme, respectively to convert the 3' end of Cp-biotin into the hydroxyl group and the 5' end of RNA into the phosphate group (FIG. 1A). After that, under in situ and non-denaturing conditions, the T4 RNA ligase is used to ligate RNAs that are spatially close to each other. Then, the total RNA is extracted by using proteinase K digestion combined with TRIzol extraction. After removing the genomic DNA and rRNA, RNA fragmentation treatment are performed. Finally, using the streptavidin magnetic beads to enrich the chimeric RNA containing C-biotin, and constructing the strand-specific library according to conventional procedures (Levin, J Z, Yassour, M., Adiconis, X., Nusbaum, C., Thompson, D A, Friedman, N., Gnirke, A., and Regev, A. (2010). Comprehensive comparative analysis of strand-specific RNA sequencing methods. Nature methods 7, 709-715.), then sequencing and analyzing the data.

We construct two RIC-seq libraries in the HeLa cells and obtain a total of 155 M (million) mappable reads. In order to facilitate data analysis and visualization, we integrate a variety of algorithms and software to establish the complete analysis process (FIG. 2A). The chimeric reads account is about 9% of all sequencing fragments, and more than 90% of the chimeric reads contain an extra "C" at the junction, which indicates the high efficiency of pCp-biotin labelling and the high specificity of streptomycin magnetic beads enrichment (FIG. 1). Each RIC-seq chimeric read represents the proximal interaction between two different RNA fragments (FIG. 1C-G). Multiple RIC-seq chimeric reads can reveal common structures or specific RNA trans interactions. The reproducibility of the RIC-seq technology is very good. The Pearson correlation coefficient between two biological replicates is 0.963 (FIG. 2B). In order to determine the false positive rate, we adopt the cell mixing strategy (Li, X., Zhou, B., Chen, L., Gou, L T, Li, H., and Fu, X D (2017). GRID-seq reveals the global RNA-chromatin interactome. Nature biotechnology 35, 940-950.), that is, the HeLa cells and the *Drosophila* S2 cells are mixed together at a ratio of 1:5, and then constructing the RIC-seq library and sequencing. The result shows that only about 0.6% of chimeric reads are derived from cross-species ligation of RNAs from *Drosophila* and human HeLa cells (FIG. 2C), indicating that the false positive rate of the RIC-seq technology is less than 1%.

Next, we symmetrically detect the resolution, sensitivity and specificity of the RIC-seq method by comparing with known RNA structures and interactions. These RNAs include microRNA, snRNA, snoRNA and lncRNA (FIG. 1C-I, FIGS. 2D-F). RIC-seq can accurately capture the classic stem-loop structure of miRNA precursor at the single-base resolution (FIG. 1C, the pCp insertion position is below), and the expression level of these miRNAs (RPM, reads per million) ranges from 0.05 to 31,067 (FIG. 1D), indicating the broad detection range of the RIC-seq technology. Unexpectedly, the position labeled by pCp-biotin is mainly enriched on the apical loop of the precursor miRNA (FIGS. 1C, 1D), indicating that the apical loop may be rarely protected by protein. Furthermore, RIC-seq successfully detects the known intermolecular and intramolecular interactions of snRNA, snoRNA, RPPH1 (the RNA component of Ribonuclease P) and TERC (telomerase RNA, data are not shown) (FIGS. 1E-I and FIGS. 2D-F). Compared with the PARIS and RAP methods (Engreitz, J. M., Sirokman, K., McDonel, P., Shishkin, A. A., Surka, C., Russell, P., Grossman, S. R., Chow, A. Y., Guttman, M., Lander, E. S. (2014). RNA-RNA interactions enable specific targeting of noncoding RNAs to nascent Pre-mRNAs and chromatin sites. Cell 159(1):188-199.); (Lu, Z., Zhang, Q. C., Lee, B., Flynn, R. A., Smith, M. A., Robinson, J. T., Davidovich, C., Gooding, A. R., Goodrich, K. J., Mattick, J. S., et al. (2016). RNA Duplex Map in Living Cells Reveals Higher-Order Transcriptome Structure. Cell 165, 1267-1279.), RIC-seq can not only capture the known U1-MALAT1 interactions, but also can identify some specific U1 and MALAT1 interaction sites in the HeLa cells (FIG. 1H). As expected, these interaction sites are conservative, contain U1 motifs, and are supported by chimeric reads (marked by arrows in FIG. 1I), suggesting potential functionality.

After fully verifying the RIC-seq method and data, we merge the data from two biological replicates and use Juicebox to create the interaction matrix genome-wide (Durand, N. C., Robinson, J. T., Shamim, M. S., Machol, I., Mesirov, J. P., Lander, E. S., and Aiden, E. L. (2016). Juicebox Provides a Visualization System for Hi-C Contact Maps with Unlimited Zoom. Cell systems 3, 99-101.), and visualize the paired interactions in the matrix by a two-dimensional heat map (IGV/Juicebox), and the intensity indicates the frequency of chimeric RNA ligation (FIG. 1J and FIG. 2A). Compared with the –pCp control (with very few chimeric reads are detected), the +pCp library contains complex intramolecular (~7 M) and intermolecular interactions (~6 M) (FIG. 2G), indicating that the RNA is not only highly structured in the cell, but also has extensive entanglement (FIG. 1J). Interestingly, some lncRNAs have extensive binding on all chromosomes, such as NEAT1 and MALAT1. In order to identify the true binding sites of these high-abundance RNAs, we perform cluster analysis on the chimeric reads, and identify 0.74 M high-confidence RNA-RNA interaction sites in the HeLa cells. Among these sites, MALAT1 and NEAT1 can not only interact with each other, but also have thousands of other targets (FIG. 1J). Consistent with recent reports (West, J. A., Davis, C. P., Sunwoo, H., Simon, M. D., Sadreyev, R. I., Wang, P. I., Tolstorukov, M. Y., and Kingston, R. E. (2014). The long noncoding RNAs NEAT1 and MALAT1 bind active chromatin sites. Molecular cell, 55, 791-802.), we also find that MALAT1 and NEAT1 are more inclined to bind to transcriptionally active genes (FIG. 2H, p<2.2e-16), and their binding motifs are highly similar (FIG. 2I).

RIC-seq reveals that MALAT1 can bind to the 5' end of NEAT1 (NEAT1_5', FIG. 1J, right). To verify these interactions, we use single-molecule in situ hybridization (smFISH) and super-resolution imaging microscope (SIM) to detect the interaction of these two lncRNAs. We find that NEAT_5' can form a loop structure, while MALAT1 has a dot-like distribution (each HeLa nucleus has 248 dots on average) (FIG. 1K and FIG. 2J). Some NEAT1 and MALAT1 fluorescence signals directly overlap (FIG. 1K box 2-4). We find that a HeLa cell has 7.5 paraspeckles on average, of which ~63.7% are co-localized with MALAT1 (FIG. 2K). In summary, the above data show that RIC-seq is a new method for identifying in situ RNA-RNA interactions with high specificity, high reproducibility and high precision.

Figures 3, 4:
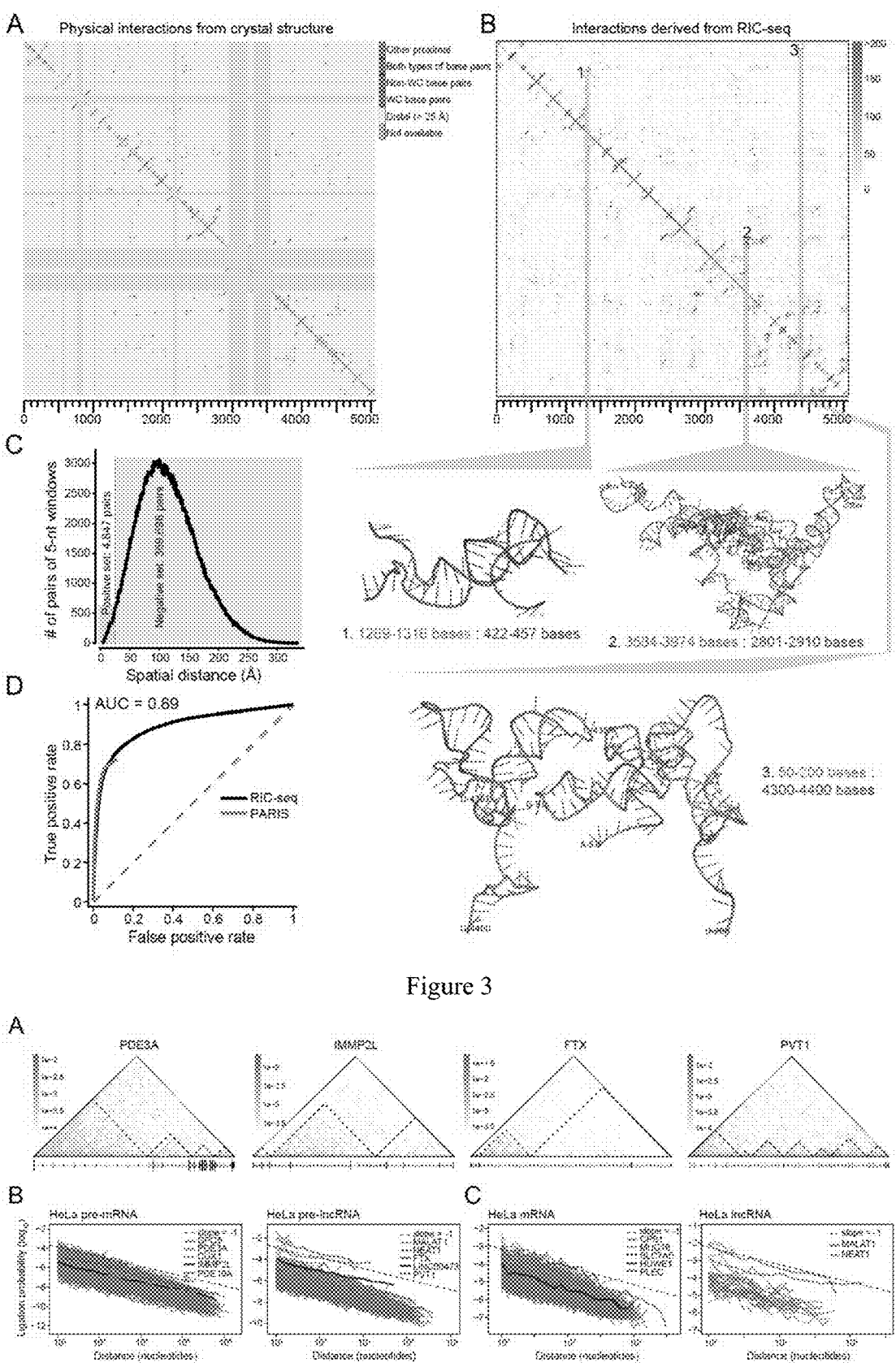
FIG. 3. RIC-seq precisely recaptures the 3D structure of 28S rRNA. (A) RNA physical interaction map inferred from the Cryo-EM structure of 28S rRNA. Spatial distances greater than 25 Å are shown in light gray (distal). For interactions within 25 Å, WC and non-WC base pairs are shown in blue and green, respectively. Interactions containing both WC and non-WC base pairs are shown in red, whereas other kinds of proximal interactions are shown in purple. Not available group means no structural data are available. (B) RNA 3D map of 28S rRNA derived from RIC-seq data in HeLa cells. Boxed regions illustrate local WC base pairs and long-range non-WC interactions. (C) The true positive and true negative datasets are generated from Cryo-EM structural data. True positive, brown; true negative, cyan. (D) RIC-seq (black line) shows better performance than PARIS (orange line) in detecting the 3D conformations of 28S rRNA. Dashed line, random. The missing part in the Cryo-EM structure was not used for generating the ROC curve.
FIG. 4. The topological organization and folding principle of RNA in vivo. (A) The topological regions (dashed triangle) observed in the precursor RNA of PDE3A, IMMP2L, FTX and PVT1. The heatmaps were created by dividing each transcript into 100 bins (1% length per bin=1 pixel) and normalizing the sum to 1.0. (B) Contact probability of each pre-mRNA and pre-lncRNA as a function of the linear distance. The slope of −1 fits a theoretical model of the fractal globule. (C) Contact probability of each mature mRNA and lncRNA as a function of the linear distance. The dashed line indicates a slope of −1.

In order to check whether RIC-seq can capture the higher-order structure of RNA, we compare the RNA proximity information detected by RIC-seq with the data obtained by the cryo-electron microscope structure of human 80S ribosomes (Anger, A. M., Armache, J. P., Berninghausen, O., Habeck, M., Subklewe, M., Wilson, D. N., and Beckmann, R. (2013). Structures of the human and *Drosophila* 80S ribosome. Nature, 497, 80-85.). First, we draw a physical interaction map of 28S rRNA based on the relative spatial distance of each pairwise 5-nt windows (FIG. 3A). We also draw a 3D map of 28S rRNA based on RIC-seq data (FIG. 3B). The two maps are highly similar at both high and low resolutions (FIG. 3A, B). Unexpectedly, RIC-seq can not only capture WC base-pairing (FIG. 3B, box 1 and box 2), but can also detect long-range loop-loop interactions, for example, the interaction between 50-200 nt and 4300-4400 nt of 28S rRNA as shown in FIG. 3B (box 3). We find that ~70% of the non-WC base-pairing interactions in the 28S rRNA structure can be detected by RIC-seq (FIG. 3A, B). These data show that RIC-seq can faithfully capture the 3D structure information of RNA.

In order to quantify the performance of RIC-seq in detecting the higher-order structure of RNA, we generate two data sets based on the cryo-electron microscope structure data of 28S rRNA: a true positive set (the 3D distance between the regions corresponding to the pairwise 5-nt windows is less than 25 Å) and a true negative set (the distance is greater than 25 Å) (4,847 vs 369,698) (FIG. 3C). The two data sets are used to evaluate the sensitivity of RIC-seq (true positive is successfully detected) and the specificity (true negative is successfully excluded). We compare the proximal interactions of 28S rRNA detected by RIC-seq with the true positive data set and true negative data set, and generate an ROC curve. The AUC value obtained by ROC analysis is 0.89, indicating that RIC-seq has high accuracy in the identification of the RNA higher-order structure (FIG. 3D, black line). As a control, we use the same data sets to evaluate the performance of PARIS. Regrettably, because a large number of 28S rRNA pairing regions and long-range interaction sites cannot be captured by PARIS, a complete curve cannot be obtained, nor the AUC value can be generated (FIG. 3D, orange line).

The high-quality RNA-RNA intramolecular interaction data generated by the RIC-seq technology allow us to detect the RNA folding principle in vivo. For this purpose, we focus on 5179 precursor mRNAs, which contain at least 100 RNA intramolecular ligation events. Interestingly, we find that there are many independent topological regions in the intron and exon regions of mRNA (FIG. 4A), their common feature is that there is unusually complex RNA-RNA interaction in a certain interval, for example, in the RNA of PDE3A and IMMP2L precursors. In order to systematically identify similar topological structure regions, we invent an iterative algorithm that can identify the boundaries of the topological regions by maximizing the ratio of the RIC-seq density within and between the regions. Compared with the mRNA precursors, similar topological regions are also evident in initially transcribed lncRNAs such as FTX and PVT1 (FIG. 4A). These data indicate that RNA is highly structured in vivo and in specific regions, and the RNA co-transcription processing may occur in independent topological regions.

The observed topological regions indicate that large RNA molecules may form complex local structures while transcribing, and then form specific higher-order structures according to a hierarchical folding pathway. However, the specific folding principle of the RNA in vivo are currently unclear. Similar to DNA polymers, RNA polymers can also exist in the form of random coils, equilibrium globules or fractal globules. The specific conformation of RNA can be deduced by calculating the ligation probability between RNA fragments at different nucleotide distances (Fudenberg, G., and Mirny, L. A. (2012). Higher-order chromatin structure: bridging physics and biology. Current opinion in genetics & development 22, 115-124.).

By using RIC-seq data and similar simulation methods (Lieberman-Aiden, E., van Berkum, N. L., Williams, L., Imakaev, M., Ragoczy, T., Telling, A., Amit, I., Lajoie, B. R., Sabo, P. J., Dorschner, M. O., et al. (2009). Comprehensive mapping of long-range interactions reveals folding principles of the human genome. Science 326, 289-293.), we detect the correlation between the contact probability (or ligation frequency) of any two fragments in the same RNA molecule and its linear distance. In the physical characteristics of polymers, if the polymer exists in a random coil state, the contact probability between two loci will rapidly decay as the linear distance increases, and the slope of the curve is expected to be −3/2 (Fudenberg, G., and Mirny, L. A. (2012). Higher-order chromatin structure: bridging physics and biology. Current opinion in genetics & development 22, 115-124.). Conversely, if the polymer exists in the form of an equilibrium globule, the contact probability will first decrease at a rate similar to that of the random coil, but then reaches equilibrium, and finally, the ligation frequency becomes independent of the linear distance (Fudenberg, G., and Mirny, L. A. (2012). Higher-order chromatin structure: bridging physics and biology. Current opinion in genetics & development 22, 115-124.). However, the random coil and equilibrium globule models do not seem to conform to the actual laws obtained by RIC-seq. Because regardless of whether introns are counted, RIC-seq data show that the contact probability between different RNA fragments gradually decreases with the increase of distance, and the slope of the curve is close to −1 (FIGS. 4B and C). This scaling agreed well with a fractal globule model (Lieberman-Aiden, E., van Berkum, N. L., Williams, L., Imakaev, M., Ragoczy, T., Telling, A., Amit, I., Lajoie, B. R., Sabo, P. J., Dorschner, M. O., et al. (2009). Comprehensive mapping of long-range interactions reveals folding principles of the human genome. Science 326, 289-293.). Therefore, based on the above data, we believe that precursor RNA may be folded in a fractal sphere conformation similar to genomic DNA in vivo. This conformation can ensure that the RNA lacks knots while maintaining the maximal packaging, and keeping the ability that the RNA can easily unfold and refold its local structures.

We next examine the conformation of mature mRNA by using chimeric reads that derived only from exons and untranslated regions. By polymer modeling, we find that the folding of the mature mRNA is power-law dependent, and the slope of the curve is also close to −1 (FIG. 4C), suggesting that the mature mRNA is also compressed into a fractal globule state. Of note, intron-lacking lncRNAs, such as NEAT1 and MALAT1, are folded similarly to pre-mRNA and intron-containing lncRNAs (FIG. 4C). In summary, these results indicate that both mRNA and ncRNA may follow a fractal globule to form complex 3D structures.

Highly structured RNA needs to interact with other RNAs to exert regulatory functions. To explore new intermolecular interaction features, we generated RNA 3D maps in diverse cell lines, including human neural progenitor cells (hNPC) and the colon adenocarcinoma cell line HT29. In addition, three common ENCODE cell lines, including the human lymphoblastoid cell line GM12878, H1 human embryonic stem cells (hESCs) and human fetal lung fibroblasts IMR-90, were selected for the potential integration of publicly available genomic data. We performed RIC-seq in these cell lines and generated 1,001 million unique reads after removing duplicates. The chimeric reads constituted 8.4% of all mappable reads. As expected, the RNA-RNA interactions in these five new cell types were also extremely complicated (FIG. 5A).

Figure 5:
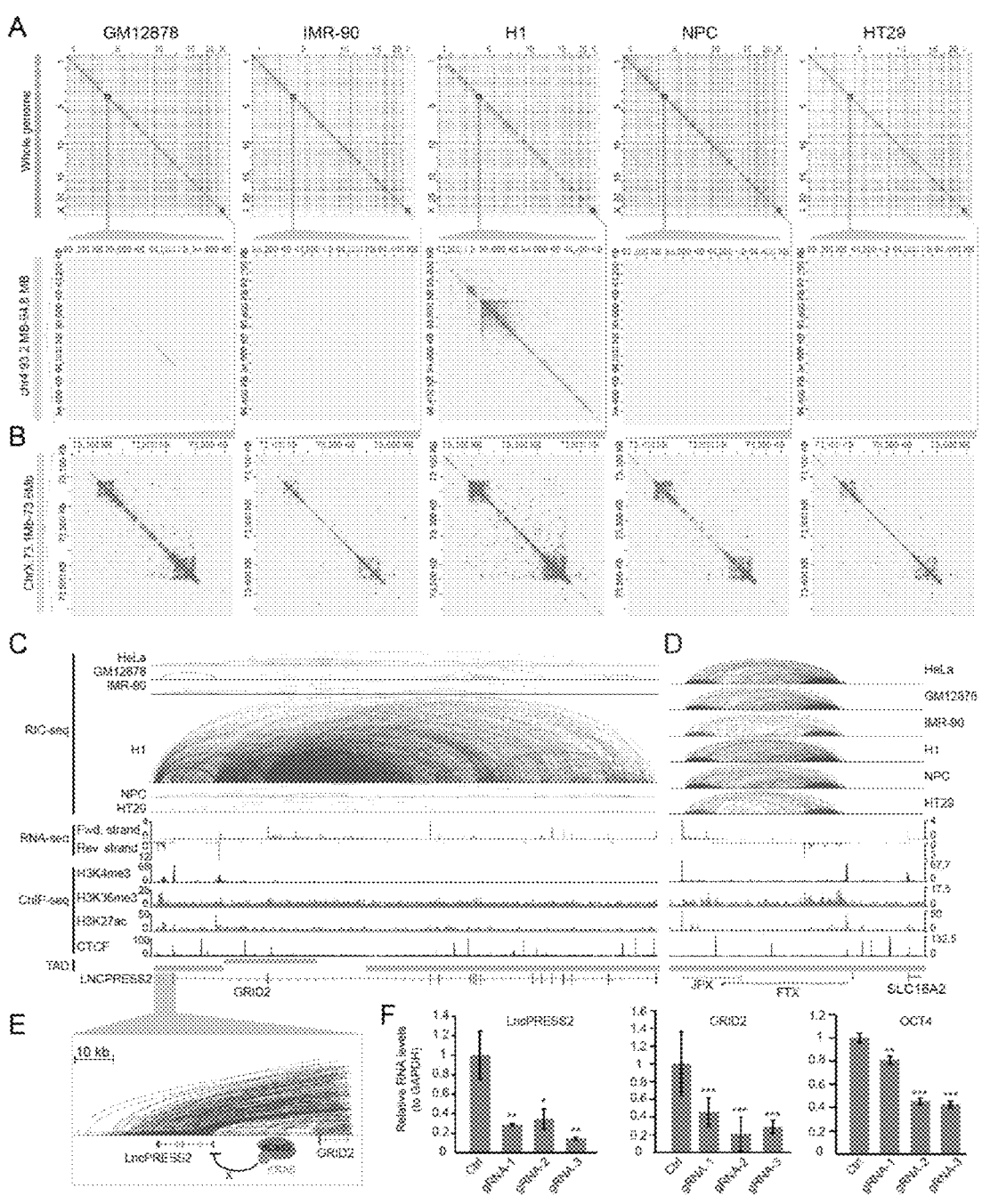
FIG. 5. Mapping RNA 3D interaction atlas in diverse cell lines. (A) The contact matrix across all chromosomes in GM12878, IMR-90, H1 hESC, NPC and HT29 cells. A magnification of specific RNA interactions in chr4:93.2 Mb-94.8 Mb is shown at the bottom. (B) Magnification of constitutive RNA-RNA interactions across 5 cell lines from (A). (C-D) The specific and constitutive RNA-RNA interactions are illustrated, respectively. The RNA-seq, ChIP-seq and TAD signals are from H1 hESC ENCODE data. (E) CRISPRi of LncPRESS2 by Cas9-KRAB. (F) Quantification of GRID2 and OCT4 expression levels upon knockdown of LncPRESS2. *P<0.05, P<0.01 and *P<0.001 by two-tailed Student's t-test (n=3).

By using these high-quality data, we identify a total of about 3 M cell-type-specific interacting clusters (fragment cutoff=2) and a large number of constitutive interaction sites in six different cell types (FIG. 5B). As exemplified by LncPRESS2 (FIG. 4A, bottom), a P53-responsive and embryonic stem cell-specific lncRNA (Jain, A. K., Xi, Y., McCarthy, R., Allton, K., Akdemir, K. C., Patel, L. R., Aronow, B., Lin, C., Li, W., Yang, L., et al. (2016). Lnc-PRESS1 Is a p53-Regulated LncRNA that Safeguards Pluripotency by Disrupting SIRT6-Mediated De-acetylation of Histone H3K56. Molecular cell 64, 967-981.), RIC-seq detects extensive interactions between LncPRESS2 and its neighboring gene GRID2 in H1 hESC (FIG. 5C). In contrast, in the ChrX: 73.1 Mb-73.6 Mb locus, we observe a constitutive interaction between lncRNA FTX and JPX (FIGS. 5B and D). It is known that these two lncRNAs play a positive regulatory role in XIST expression (Carmona, S., Lin, B., Chou, T., Arroyo, K., and Sun, S. (2018). LncRNA Jpx induces Xist expression in mice using both trans and cis mechanisms. PLoS genetics 14, e1007378; Chureau, C., Chantalat, S., Romito, A., Galvani, A., Duret, L., Avner, P., and Rougeulle, C. (2011). Ftx is a non-coding RNA which affects Xist expression and chromatin structure within the X-inactivation center region. Human molecular genetics 20, 705-718.; Sun, S., Del Rosario, B. C., Szanto, A., Ogawa, Y., Jeon, Y., and Lee, J. T. (2013). Jpx RNA activates Xist by evicting CTCF. Cell 153, 1537-1551.; Tian, D., Sun, S., and Lee, J. T. (2010). The long noncoding RNA, Jpx, is a molecular switch for X chromosome inactivation. Cell 143, 390-403.), and have been shown critical for XIST-mediated X-chromosome silencing. The interaction between these two lncRNAs suggests that they may function as a complex to regulate XIST. These cell type-specific and constitutive interactions further highlight the specificity of the RIC-seq method and show that RIC-seq can be used to identify lncRNA targets in living cells.

In order to further verify the function of the LncPRESS2-GRID2 interaction, we adopt the Cas9-KRAB-mediated lncRNA silencing strategy (Gilbert, L. A., Larson, M. H., Morsut, L., Liu, Z., Brar, G. A., Torres, S. E., Stern-Ginossar, N., Brandman, O., Whitehead, E. H., Doudna, J. A., et al. (2013). CRISPR-mediated modular RNA-guided regulation of transcription in eukaryotes. Cell 154, 442-451.), wherein sgRNA can specifically target Cas9-KRAB directly to a promoter region of lncRNA, where KRAB functions as a transcription inhibitor of RNA polymerase II (FIG. 5E), thus efficiently block the transcription of the specific lncRNA. Upon the depletion of LncPRESS2 with three different sgRNAs, the GRID2 levels were dramatically decreased (FIG. 5F), indicating that the LncPRESS2 can positively regulate the expression of GRID2 even though the linear distance is greater than 25 kb. Surprisingly, in Lnc-PRESS2 knockdown cells, the expression of a stem cell pluripotency key factor OCT4 is significantly decreased (FIG. 5F), which means that the LncPRESS2 mediated GRID2 regulation may be closely related to stemness. The above data show that the RIC-seq technology can indeed identify functional lncRNA targets.

Figures 6, 7:
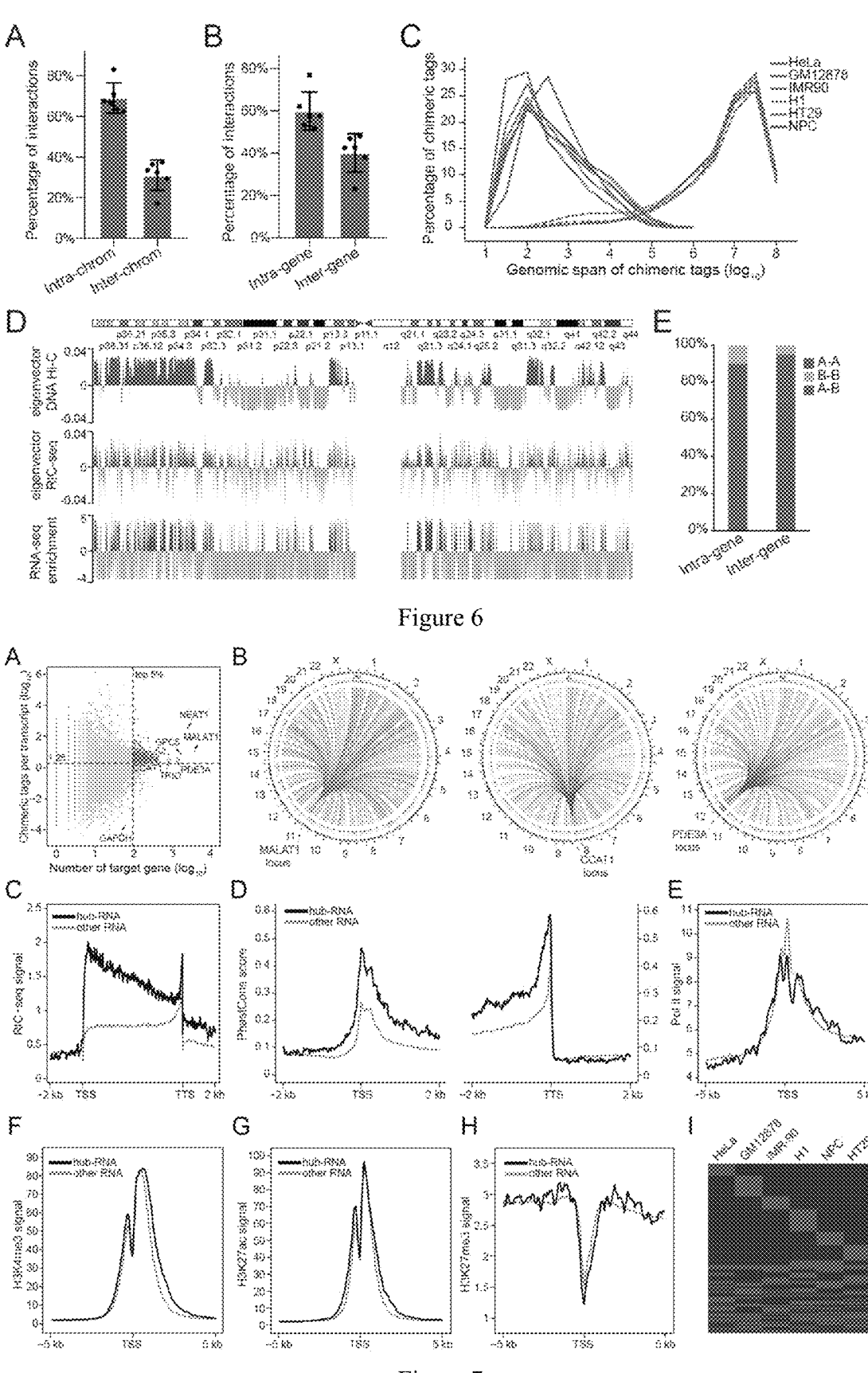
FIG. 6. The characteristics of in situ RNA-RNA interactions. (A) The percentages of intra- and interchromosomal RNA-RNA interactions across 6 different cell types. (B) The percentages of intra- and intergene RNA-RNA interactions. (C) The percentage and span distance of the intrachromosomal chimeric reads in 6 different cell types. Solid and dashed lines denote intragene or intergene interactions, respectively. (D) The Hi-C, RIC-seq and RNA-seq compartments in chromosome 1. Data for GM12878 are shown. (E) The percentages of RNA-RNA interactions between different compartments for intra- and intergenes.
FIG. 7. Cell type-specific hub-RNAs in the human genome. (A) Each RNA in HeLa cells is sorted based on its chimeric tag intensity and the number of interacting genes. GAPDH served as a negative control. (B) Circos plot of MALAT1, CCAT1 and PDE3A-interacting RNAs across 23 chromosomes. The red arrow marks gene location. (C) Meta-analysis of the RIC-seq intensity and distribution for hub-RNAs and other RNAs. RIC-seq signals surrounding the transcription start site (TSS) and transcription termination site (TTS) were plotted. (D) Hub-RNAs are more conserved than other RNAs. (E-H) ChIP-seq signals of RNA polymerase II, H3K4me3, H3K27ac and H3K27me3 on hub-RNA and other RNAs. (I) The majority of hub-RNAs are specific to cell type.

In order to reveal the general characteristics of RNA-RNA interactions in different cell types, we first calculate the frequency of intrachromosomal and interchromosomal interactions respectively. By using RIC-seq data generated in the above six cell types, we find that $\sim_{70}\%$ of RNA-RNA interactions occur within the same chromosome, while the remaining ~30% occur between different chromosomes (FIG. 6A). As RNA-RNA interactions can occur both in cis and in trans, we also calculate the frequency of intragene and intergene interactions respectively. Similarly, about 60% of chimeric reads shows cis-interaction within the genes, and can be used to deduce the RNA 3D architecture; the remaining 40% exhibits trans-RNA-RNA interaction properties (FIG. 6B), which indicates that a large number of RNAs in the cells can span a long distance to interact with other RNAs in the same chromosome or different chromosomes. If we only count the chimeric reads in the same chromosome, this trend is also obvious, wherein we detect two obvious peaks: the first peak corresponds to the intragene interaction, which can span hundreds of nucleotides; and the second peak corresponds to the intergene interaction, which spans a distance of more than 1 Mb (FIG. 6C).

Chromatin is heavily packed in vivo and organized into compartments A and B (Lieberman-Aiden, E., van Berkum, N. L., Williams, L., Imakaev, M., Ragoczy, T., Telling, A., Amit, I., Lajoie, B. R., Sabo, P. J., Dorschner, M. O., et al. (2009). Comprehensive mapping of long-range interactions reveals folding principles of the human genome. Science 326, 289-293.), which are represented by different transcriptional activities. Similar to the organization of chromatin, RNA interactions also seem to be compartmentalized and can largely recapitulate the compartment of DNA (FIG. 6D), which indicates that the RNAs in the same compartment may be more tend to interact with each other due to spatial proximity. We next quantify the interactions between different compartments. Interestingly, among intragene interactions, chimeric reads are mainly enriched in the same compartment, and A to A can account for ~90% of the total chimeric reads (FIG. 6E), which may be caused by the active transcription of the compartment A and the spatial distances within these genes are relatively closer. In contrast, for intergene interactions, the interaction of compartments A to A decreases to about 65%, but the interaction of the compartments A to B increases to ~30% (FIG. 6E), which indicates that such trans RNA interactions may have some unknown functions and may regulate the activity of the genes in the compartment B.

Since the trans RNA-RNA interactions can span more than 1 Mb and even across different chromosomes, we next sorted the RNA-RNA interactions based on two criteria: the number of target genes and the interaction density determined by normalizing chimeric reads to RNA expression levels. Interestingly, this analysis unexpectedly reveals –500 highly abundant RNA-RNA interaction hubs in the HeLa cells (FIG. 7A), including well-known lncRNAs such as MALAT1, NEAT1, CCAT1, and PVT1. Unexpectedly, many protein-coding genes also show complex RNA-RNA interactions, such as PDE3A, GPC5, and TRIO (FIG. 7A). The interaction patterns and genomic locations of MALAT1, CCAT1 and PDE3A are visualized as Circos plots (FIG. 7B). Since the RNAs transcribed from these loci seem to function as a hub to organize the RNA-RNA interactions on a genome-wide scale, we term these RNAs as hub-RNAs, which include hub-mRNAs and hub-lncRNAs.

In order to characterize the characteristics of hub-RNA, we divide all RNAs expressed in the HeLa cells into two groups: hub-RNAs and other RNAs. Based on the RIC-seq signals, we find that hub-RNAs have stronger trans RNA-RNA interactions and show significant enrichment at gene bodies (FIG. 7C). In addition, these hub-RNAs are evolutionarily more conserved than the other RNAs (FIG. 7D), and are also actively transcribed. The RNA polymerase II is also enriched in the TSS (transcription starting site) regions of these genes (FIG. 7E). Correspondingly, the occupancy of the active histone markers H3K4me3 (FIG. 7F) and H3K27ac (FIG. 7G) is slightly higher. In contrast, repressive histone marker H3K27me3 has a slightly lower signal (FIG. 7H). At the same time, we find that the hub-RNAs are cell-type-specific (FIG. 7I). Therefore, RIC-seq unexpectedly reveals a group of tissue-specific hub-RNAs that may play an important role in gene regulation.

In order to investigate the roles of the hub-RNAs, we chose CCAT1 for further analysis because of its extensive trans-RNA interactions (FIG. 7B) and potential super-enhancer activity (Hnisz, D., Abraham, B. J., Lee, T. I., Lau, A., Saint-Andre, V., Sigova, A. A., Hoke, H. A., and Young, R. A. (2013). Super-enhancers in the control of cell identity and disease. Cell 155, 934-947.; Loven, J., Hoke, H. A., Lin, C. Y., Lau, A., Orlando, D. A., Vakoc, C. R., Bradner, J. E., Lee, T. I., and Young, R. A. (2013). Selective inhibition of tumor oncogenes by disruption of super-enhancers. Cell 153, 320-334.). CCAT1 localizes to the human 8q24 gene desert and is abnormally highly expressed in a variety of cancers such as colorectal cancer, prostate cancer and hepatocellular cancer (Chen, H., He, Y., Hou, Y. S., Chen, D. Q., He, S. L., Cao, Y. F., and Wu, X. M. (2018a). Long non-coding RNA CCAT1 promotes the migration and invasion of prostate cancer PC-3 cells. European review for medical and pharmacological sciences 22, 2991-2996.; Deng, L., Yang, S. B., Xu, F. F., and Zhang, J. H. (2015). Long noncoding RNA CCAT1 promotes hepatocellular carcinoma progression by functioning as let-7 sponge. Journal of experimental & clinical cancer research: CR 34, 18.; Tseng, Y. Y., Moriarity, B. S., Gong, W., Akiyama, R., Tiwari, A., Kawakami, H., Ronning, P., Reuland, B., Guen-
ther, K., Beadnell, T. C., et al. (2014). PVT1 dependence in
cancer with MYC copy-number increase. Nature 512,
82-86.; Xiang, J. F., Yin, Q. F., Chen, T., Zhang, Y., Zhang,
X. O., Wu, Z., Zhang, S., Wang, H. B., Ge, J., Lu, X., et al.
(2014). Human colorectal cancer-specific CCAT1-L
lncRNA regulates long-range chromatin interactions at the
MYC locus. Cell research 24, 513-531.). In colorectal
cancer cells, researchers report a CCAT1 transcript with an
additionally extended 3' end, and find that the transcript can
regulate spatial interactions between the promoter and
enhancer of the MYC gene (Xiang, J. F., Yin, Q. F., Chen,
T., Zhang, Y., Zhang, X. O., Wu, Z., Zhang, S., Wang, H. B.,
Ge, J., Lu, X., et al. (2014). Human colorectal cancer-
specific CCAT1-L lncRNA regulates long-range chromatin
interactions at the MYC locus. Cell research 24, 513-531.),
but the precise mechanism is unknown.

Figure 8:
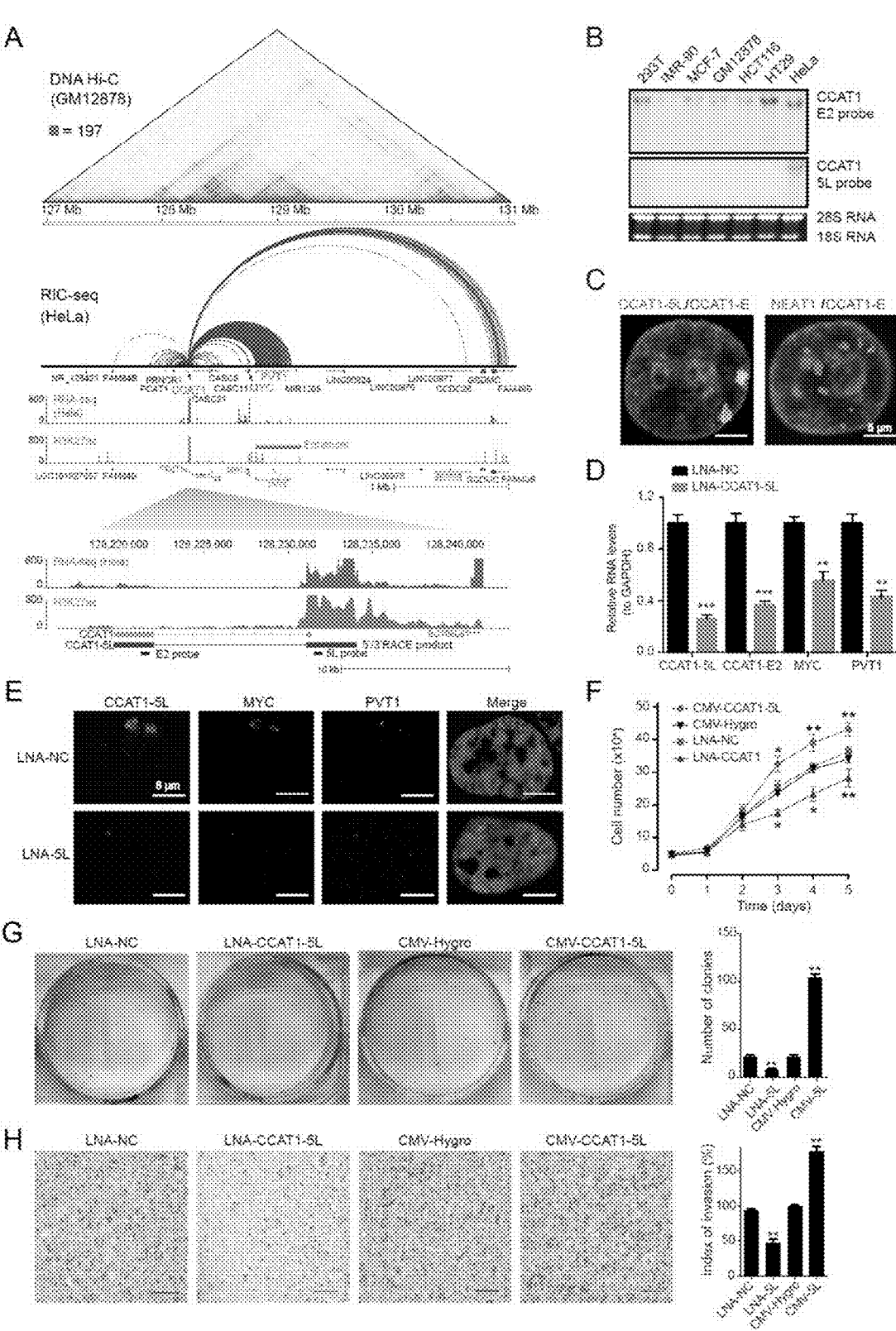
FIG. 8. Hub-RNA CCAT1-5L boosts MYC gene expression by synergizing with MYC promoter and enhancer RNA. (A) Snapshot of the RIC-seq, RNA-seq and H3K27ac signals on 8q24. The 5' and 3' RACE-mapped CCAT1 transcript is shown at the bottom. Northern blot probes are labeled as black lines. CCAT1, MYC and PVT1 genes are marked in red. The chimeric reads between CCAT1-5L and MYC are shown in red. (B) Northern blot analysis of CCAT1-5L expression across diverse cell lines. The 5L probe detects only CCAT1-5L in HeLa cells. The 18S and 28S rRNAs served as loading controls. (C) CCAT1-5L is localized in the nucleus by smFISH. CCAT1-5L is shown in red, CCAT1-Exon2 probes (CCAT1-E) are shown in green, the NEAT1 5' region is shown in red, and DAPI is shown in blue. Scale bar: m. (D) The MYC expression was reduced upon knockdown of CCAT1 by 5L-specific LNA oligos. The 5L- and Exon2-specific primers were used to monitor CCAT1 levels. (E) CCAT1-5L, MYC promoter and MYC enhancer RNA are colocalized by smFISH. CCAT1-5L is pseudocolored in red, MYC in green and PVT1 in yellow. Scale bar: 5 m. (F) The cell proliferation rate was measured upon the depletion or ectopic expression of CCAT1-5L. (G) Knockdown or ectopic expression of CCAT1-5L affects colony formation. (H) CCAT1-5L is critical for cell metastasis in a transwell assay. Scale bar: 50 m. *P<0.05 and **P<0.01 by two-tailed Student's t-test (n=3).

Because the CCAT1 partially overlaps with the reported
super-enhancer (Khan, A., and Zhang, X. (2016). dbSUPER:
a database of super-enhancers in mouse and human genome.
Nucleic acids research 44, D164-171.), by examining the
RIC-seq and RNA-seq data in the HeLa cells, we unexpect-
edly find that CCAT1 may have a transcript with an addi-
tionally extended 5' end, instead of the additionally extended
3' end previously reported in colon cancer (FIG. 8A). The 5' and 3' RACE mapping results in the HeLa cells also confirm
the additionally 5' extension (FIG. 8A, marked in brown at
the bottom), which directly overlaps with a super-enhancer
and has a total length of ~4,700 nt. We refer this lncRNA as
CCAT1-5L. Northern blotting with the Exon2 (E2) probe
(see FIG. 8A) confirms that CCAT1 is expressed in different
cell types, while the 5L-specific probe detects CCAT1-5L
only in HeLa cells (FIG. 8B), indicating that CCAT1-5L
may be a specific transcript in cervical cancer, which is
further confirmed in the RNA-seq data from cervical cancer
patients (data are not shown).

smFISH shows that CCAT1-5L is a nuclear-retained
lncRNA and forms 2-3 spots in each nucleus (FIG. 8C).
CCAT1-5L seems to be functional, because most of the RNA
interactions from CCAT1 to other regions of the 8q24 "gene
desert" were found to originate from the first exon and an
additional 5' end extension region (FIG. 8A). In addition, we
detect extensive long-range RNA-RNA interactions between
CCAT1-5L, MYC promoter-RNA and PVT1. More impor-
tantly, CCAT1-5L binding sites observed in the PVT1 locus
are mainly located in the intron regions containing the MYC
enhancers (FIG. 8A, orange line). The above data suggest
that CCAT1-5L may function as a super-enhancer RNA that
interacts with the promoter and enhancer RNAs to regulate
the expression of the MYC oncogene.

We next explore whether CCAT1-5L can directly regulate
the MYC expression. When CCAT1-5L is knocked down by
two LNA oligos targeting the 5' end extension region (FIG.
8D), the RNA level of MYC is significantly reduced by
~40% (FIG. 8D), indicating that CCAT1-5L can indeed
regulate the MYC expression in the HeLa cells. Unexpect-
edly, the expression level of PVT1, a positive regulator of
MYC (Tseng, Y. Y., Moriarity, B. S., Gong, W., Akiyama, R., Tiwari, A., Kawakami, H., Ronning, P., Reuland, B., Guen-
ther, K., Beadnell, T. C., et al. (2014). PVT1 dependence in
cancer with MYC copy-number increase. Nature 512,
82-86.), is also greatly reduced (FIG. 8D). Therefore, we
hypothesize that CCAT1-5L hub-lncRNA may synergize
with the promoter and enhancer RNAs of MYC to coordi-
nate their expression levels.

To test this hypothesis, we first check whether CCAT1-
5L, MYC promoter and MYC enhancer RNAs are colocal-
ized in vivo. To this end, we first synthesize smFISH probes,
respectively targeting the CCAT1-5L part detected by RIC-
seq, the first exon and first intron of MYC, and the enhancer
located in the PVT1 intron. The results show that the three
RNAs show perfect colocalization (FIG. 8E). This further
confirms the regulating role of CCAT1-5L on MYC and
PVT1. In addition, after the CCAT1-5L is knocked down in
the LNA oligonucleotide, the co-localization pattern
between MYC promoter and enhancer RNAs does not
change (FIG. 8E).

Since CCAT1-5L is highly expressed in cervical cancer
patients, we next check whether CCAT1-5L can promote
cell proliferation and metastasis, which are two landmarks of
cancer (Hanahan, D., and Weinberg, R A (2011). Hallmarks
of cancer: the next generation. Cell 144, 646-674.). In
contrast to the LNA controls, knockdown of CCAT1-5L by
the 5L-specific LNA oligos in HeLa cells significantly
reduces the proliferation rate (FIG. 8F); and on the contrary,
ectopic expression of CCAT1-5L with a lentiviral plasmid
can significantly enhance cell proliferation (FIG. 8F), which
is consistent with the oncogenic effect of CCAT1-5L. The
colony formation assay further confirms the effect of
CCAT1-S on cell proliferation (FIG. 8G). In order to detect
whether CCAT1-5L can affect cell metastasis and invasion,
we perform a cell invasion assay using a transwell insert and
find that knockdown of CCAT1-5L significantly reduces the
metastasis ability of HeLa cells, while the overexpression of
CCAT1-5L significantly increases invasion and metastasis
(FIG. 8H). In summary, these data indicate that CCAT1-5L
hub-lncRNA can directly regulate the MYC expression to
promote tumorigenesis.

INDUSTRIAL APPLICATION

The method for capturing an RNA in situ higher-order
structure and interaction provided by the present invention
can process the intracellular RNA in situ without destroying
the cell structure and maintaining the integrity of the cell,
and capture RNA intramolecular and intermolecular inter-
actions in the physiological state. The method for capturing
RNA in situ higher-order structure and interaction provided
by the present invention uses pCp-biotin to label RNA ends,
and performs in situ ligation under non-denaturing condi-
tions, thereby greatly improving the labeling efficiency and
reducing the non-specific ligation between molecules; and
chimeric RNAs labeled with C-biotin are enriched by C1
magnetic beads for constructing a library, so that the chi-
meric RNA can be efficiently enriched, the fraction of usable
data is increased, and the sequencing cost is reduced.

The invention claimed is:

1. A method for capturing an RNA higher-order structure in situ and/or verifying in situ RNA-RNA interaction, comprising the following steps:

(1) treating cell or tissue sample to fix protein-mediated RNA-RNA proximal interaction;

(2) performing membrane permeabilization while keeping the cell intact;

(3) degrading free RNAs that are not protected by protein;

(4) labeling the 3' end of RNA protected by the protein with a pCp-Marker 1 and performing proximal ligation in situ;

(5) purifying chimeric RNA containing C-marker 1 after cells are digested; and constructing strand-specific library;

(6) performing high-throughput sequencing;

wherein in the step (2), the permeabilization solution used during the membrane permeabilization is a Permeabilization buffer; and the solvent of the Permeabilization solution is 10 mM Tris-HCl buffer with pH 7.5, and the solute and concentration are as follows: 10 mM of NaCl, 0.5% (v/v) octylphenoxypolyethoxyethanol, 0.3% (v/v) Polyethylene glycol tert-octylphenyl ether, 0.1% (v/v) Polysorbate-20, 1×protease inhibitors and 2 U/ml of RNase Inhibitor.

2. The method according to claim 1, wherein the step (2) is performed according to a method comprising:

(b1) placing the cell or tissue sample treated in the step (1) in the Permeabilization buffer at 0° C.-4° C. for 15 minutes.

3. The method according to claim 2, wherein after the step (b1), the method further comprises:

(b2) washing the cell or tissue sample treated in the step (b1) with 1×PNK solution, wherein a solvent of 1×PNK solution is 50 mM of Tris-HCl buffer with pH 7.4, and the solutes and concentration are as follows: 10 mM of MgCl₂, 0.1 mg/ml of BSA, and 0.2% (v/v) NP-40.

* * * * *

SEQUENCE LISTING

<160> NUMBER OF SEQ ID NOS: 2

<210> SEQ ID NO 1
<211> LENGTH: 58
<212> TYPE: DNA

-continued

```
<213> ORGANISM: Artificial sequence
<220> FEATURE:
<223> OTHER INFORMATION: Synthetic

<400> SEQUENCE: 1
aatgatacgg cgaccaccga gatctacact ctttccctac acgacgctct tccgatct          58

<210> SEQ ID NO 2
<211> LENGTH: 66
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (26)..(32)
<223> OTHER INFORMATION: n is a or t or c or g

<400> SEQUENCE: 2
caagcagaag acggcatacg agatannnnn nngtgactgg agttcagacg tgtgctcttc          60
cgatct                                                                   66
```